United States Patent [19]

Jackle et al.

[11] 4,136,092
[45] Jan. 23, 1979

[54] POLYURETHANE CURING AGENTS

[75] Inventors: William A. Jackle, Newtown, Pa.; Michael P. Mazzeo, Hightstown, N.J.; Marina N. Gillis, Yardley, Pa.

[73] Assignee: Thiokol Corporation, Newtown, Pa.

[21] Appl. No.: 685,215

[22] Filed: May 11, 1976

Related U.S. Application Data

[63] Continuation-in-part of Ser. No. 585,150, Jun. 9, 1975, abandoned.

[51] Int. Cl.² .............................................. C08G 71/04
[52] U.S. Cl. ...................................... 528/60; 528/62; 528/28
[58] Field of Search .... 260/75 NC, 75 NM, 77.5 AC, 260/77.5 AQ

[56] References Cited

U.S. PATENT DOCUMENTS

| | | | |
|---|---|---|---|
| 3,328,321 | 6/1967 | Wismer et al. | 260/75 NM X |
| 3,399,151 | 8/1968 | Kaiser | 260/77.5 AQ X |

FOREIGN PATENT DOCUMENTS 889204  2/1962  United Kingdom.

Primary Examiner—Sandra M. Person
Attorney, Agent, or Firm—Stanley A. Marcus; Royal E. Bright

[57] ABSTRACT

Isocyanate-terminated prepolymers can be cured with di- and triamino-s-triazines of formula

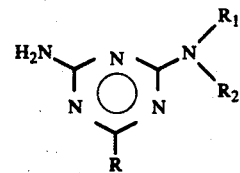

where R is

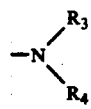

$-S-R_5$; $-O-R_6$ or

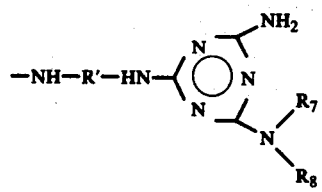

where at least one of $R_1$, $R_2$, $R_3$ and $R_4$ is hydrogen; $R_1$, $R_2$, $R_3$, $R_4$, $R_5$, $R_6$, $R_7$ and $R_8$ are hydrogen or an optionally substituted aromatic or aliphatic group and R' is the divalent residue of an organic diamine, the residue of an organic diisocyanate, or the residue of an organic diepoxide.

13 Claims, No Drawings

POLYURETHANE CURING AGENTS

This application is a Continuation-in-Part of application Ser. No. 585,150, filed June 9, 1975 now abandoned.

BACKGROUND OF THE INVENTION 4,4'-Methylenebis (2-chloroaniline) is a well-known and valuable curing agent for polyurethane prepolymers because of the properties it imparts to the polyurethane product. In commercial practice, for example in the preparation of urethane castings, 4,4'-methylene-bis (2-chloroaniline) is usually mixed as a molten fluid into a heated polyurethane prepolymer. Melting the solid diamine is inconvenient and extremely hazardous since 4,4'-methylenebis (2-chloroaniline) has recently been classified as a suspected carcinogen and its use has been severely curtailed. Furthermore, the addition of molten 4,4'-methylenebis (2-chloroaniline) to the preheated polyurethane prepolymer results in a polyurethane which has a short pot life. That is, there is insufficient time in many cases for mixing the molten diamine with the polyurethane prepolymer and pouring of the mixture into molds before the mixture becomes unpourable. To overcome the difficulties associated with incorporating solid 4,4'-methylenebis (2-chloroaniline) into a polyurethane prepolymer, there have been proposed a variety of techniques for curing polyurethane prepolymers with compositions containing 4,4'-methylenebis (2-chloroaniline) to obtain polyurethane compositions with satisfactory pot life and good physical properties. Some of these techniques are illustrated in U.S. Pat. Nos. 3,718,619 and 3,718,624. The synthesis and use of compounds analogous to 4,4'-methylenebis (2-chloroaniline) is described in U.S. Pat. Nos. 3,408,301 and 3,728,310. The use of bis(aminoarylene) sulfones, such as bis(aminophenylene) sulfone to cure urethane prepolymers is described in U.S. Pat. No. 3,355,435.

DESCRIPTION OF THE PRIOR ART

U.S. Pat. No. 3,726,835 discloses storage-stable polyurethane prepolymers in which the stabilizer is melamine or dicyandiamide. While the compositions are useful, they must be heated to temperatures on the order of 300° F. (148.8° C.) to cure. Melamine does not melt at the temperatures normally used in conjunction with urethane casting materials 212-250° F. (100°-121.1° C.) and presents handling disadvantages.

U.S. Pat. No. 3,438,916 discloses that certain N-chlorinated melamines in combination with a long chain fatty acid and a zinc salt are activators for known accelerators in vulcanizing sulfur-vulcanizable polyurethanes. Vulcanization temperature of such activated polyurethane compositions are 280° to 315° F. (137.8 to 157.2° C.).

German Pat. No. 1,284,020 discloses the use of s-triazines of the formula

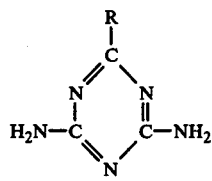

wherein R is hydrogen, a halogen atom, an alkyl radical, an aryl radical or an alkyl or aryl radical substituted by halogen. These compounds are used to cure isocyanate terminated polyesters for spinning thread. Cure is accomplished at the ideal thread spinning temperature of 60–100° C. (140–212° F.) and the products are stated to be highly elastic threads.

U.S. Pat. Nos. 3,301,823 and 3,367,899 disclose the use of dihydrazino-mono and bis -s-triazino compounds for reaction with isocyanate-terminated urethane prepolymers to form polyurethane elastomers. Both references require the reaction to take place in a polar solvent such as dimethylformamide.

SUMMARY OF THE INVENTION

The invention is based on the discovery that certain substituted di- and triamino-s-triazines, melting in the range of about 70° C. to about 180° C. (158° to about 350° F.), are effective curing agents for polyurethanes and provide cured polyurethane compositions, particularly cast or molded compositions, which display unexpected and valuable properties.

One well-known means for curing polyurethanes involves combining the curing agent with the urethane prepolymer at a temperature of 70° to 100° C. (158° to 230° F.) and curing the mixture at a temperature of 90° to 150° C. (194° to 302° F.). So that high mixing or processing temperatures are not necessary in this operation it is advantageous that the curing agent be a liquid, a low-melting solid or a solid which when melted exhibits good supercooling properties. If the curing agent solidifies before it is completely blended into the polymer, or crystallizes from the blend, an improper cure will be obtained.

The substituted di- and triamino-s-triazines of this invention provide ease and convenience of processing at conventional temperatures and fabrication conditions, useful pot life, cured articles having excellent physical properties and are free of the toxicological disadvantages that characterize 4,4'-methylenebis (2-chloroaniline).

In one aspect, this invention relates to curable compositions comprising an isocyanate-terminated polyurethane prepolymer and a substituted di- or triamino-s-triazine. In another aspect, this invention relates to the method of making a cured polyurethane product which comprises mixing an isocyanate-terminated polyurethane prepolymer with a cure-effective amount of a substituted di- or triamino-s-triazine and heating the mixture to cure the product. In yet another aspect this invention relates to a cured polyurethane product containing the residue of a di- or triamino-s-triazine, as defined. In still another aspect, this invention relates to a urethane elastomer comprising the reaction product of an excess of an organic disocyanate, a material selected from the class consisting of polyester diols, polyester amide diols, and polyether diols and a substituted di- or triamino-s-triazine.

DETAILED DESCRIPTION OF THE INVENTION

It has now been found that isocyanate-terminated polyurethane prepolymers can be cured with substituted di- and triamino-s-triazines of general formula:

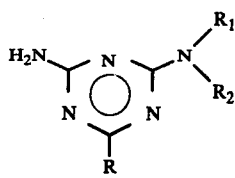

where R is

—S—R₅;
—O—R₆ or

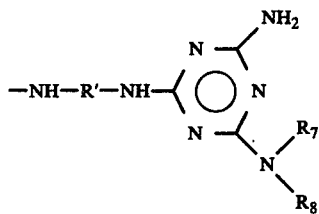

at least one of $R_1$, $R_2$, $R_3$ and $R_4$ is hydrogen, $R_1$, $R_2$, $R_3$, $R_4$, $R_5$, $R_6$, $R_7$ and $R_8$ each independently is hydrogen, alkyl of 1 to 24 carbon atoms, alkenyl of 3 to 24 carbon atoms, alkynyl of 3 to 24 carbon atoms, or cycloalkyl of 3 to 10 carbon atoms said alkyl, alkenyl, alkynyl or cycloalkyl being unsubstituted or substituted by:
  alkoxy of 1 to 18 carbon atoms,
  the acyl residue of an aliphatic carboxylic acid of 2 to 18 carbon atoms or of an aromatic carboxylic acid containing 6 to 10 carbon atoms in the aromatic nucleus,
  acyloxy, where the acyl moiety is as previously defined,
  carbalkoxy of 3 to 20 carbon atoms,
  carboaryloxy where the aryl moiety contains 6 to 10 carbon atoms in the aromatic nucleus,
  alkylcarbonyldioxy containing 1 to 8 carbon atoms in the alkyl moiety,
  arylcarbonyldioxy where the aryl moiety contains 6 or 10 carbon atoms in the aromatic nucleus,
amino, carbamoyl, sulfamoyl that are unsubstituted or substituted on the nitrogen atom by
  1 or 2 radicals independently selected from alkyl of 1 to 18 carbon atoms, cycloalkyl of 3 to 8 carbon atoms, aryl of 6 or 10 carbon atoms in the aryl nucleus and acyl as previously defined and where said radicals are further unsubstituted or substituted by chloro, fluoro, iodo, bromo, amino, hydroxyl, lower alkoxy, carbamoyl, sulfamoyl, lower alkylthio, perfluoroalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano,
chloro, fluoro, bromo, iodo, perhaloalkyl of 1 to 12 carbon atoms,
oxo, nitro, cyano, thiocyano,
alkylthio of 1 to 18 carbon atoms,
arylthio of 6 to 10 carbon atoms in the aryl nucleus,
alkylsulfinyl of 1 to 18 carbon atoms,
arylsulfinyl of 6 to 10 carbon atoms in the aryl nucleus,
alkylsulphonyl of 1 to 18 carbon atoms,
arylsulphonyl or 6 or 10 carbon atoms in the aryl nucleus,
alkylphosphoryl of 1 to 18 carbon atoms,
arylphosphoryl of 6 or 10 carbon atoms in the aryl nucleus,
alkylthiophosphoryl of 1 to 18 carbon atoms,
arylthiophosphoryl of 6 or 10 carbon atoms in the aryl nucleus,
cycloalkyl of 3 to 10 carbon atoms,
cycloalkyloxy of 3 to 10 carbon atoms,
phenyl or naphthyl,
acylamino where the acyl moiety is as previously defined,
alkylureido of 1 to 18 carbon atoms,
arylureido of 6 or 10 carbon atoms in the aryl nucleus,
silyl of formula

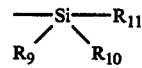

where $R_9$, $R_{10}$ and $R_{11}$ each independently is branched or unbranched alkyl of 1 to 6 carbon atoms, cycloalkyl of 3 to 7 carbon atoms, phenylalkylene of 1 to 6 carbon atoms in the alkyl group, phenyl or alkyl phenylene of 1 to 6 carbon atoms in the alkyl group,
or where $R_1$, $R_2$, $R_3$, $R_4$, $R_5$, $R_6$, $R_7$ and $R_8$ each independently is aryl of 6 or 10 carbon atoms that is unsubstituted or substituted by one to three of:
alkyl of 1 to 18 carbon atoms
cycloalkyl of 3 to 8 carbon atoms
alkoxy of 1 to 18 carbon atoms
chloro, bromo, iodo, fluoro, perhaloalkyl of 1 to 12 carbon atoms
nitro, cyano, thiocyano, alkylthio of 1 to 18 carbon atoms,
arylthio of 6 or 10 carbon atoms in the aryl nucleus
amino, sulfamoyl or carbamoyl, said amino, sulfamoyl or carbamoyl containing one or two substituents on the nitrogen atom selected from alkyl of 1 to 18 carbon atoms, cycloalkyl of 3 to 8 carbon atoms, aryl of 6 or 10 carbon atoms in the aryl nucleus or acyl as previously defined, and where said nitrogen substituents are further unsubstituted or substituted by chloro, fluoro, iodo, bromo, amino, lower alkoxy, carbamoyl, sulfamoyl, lower alkylthio, perfluoroalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano,
the acyl residue of an aliphatic carboxylic acid of 2 to 18 carbon atoms or of an aromatic carboxylic acid containing 6 or 10 carbon atoms in the aryl nucleus,
carbalkoxy of 2 to 18 carbon atoms,
carboaryloxy containing 6 or 10 carbon atoms in the aryl nucleus,
acylamino where acyl is as previously defined,
phenyl, naphthyl, phenoxy, naphthoxy
phenylthio, phenylimino, phenylmethylene,
phenylsulfonyl,
and where said hydrocarbon substituents on the alkyl, alkenyl, alkynyl, cycloalkyl and aryl groups can be further substituted by chloro, fluoro, iodo, bromo, amino, hydroxyl, lower alkoxy, carbamoyl, sulfamoyl, lower alkylthio, perfluoroalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano, or where one of the pairs of $R_1$-$R_2$, $R_3$-$R_4$ or one or both of the pairs $R_1$-$R_2$ and $R_7$-$R_8$ can together with their associated nitrogen atoms from morpholinyl, piperidyl, piperazyl, or pyrrolidinyl;

and where R' is
  alkylene of 2 to 24 carbon atoms, alkenylene of 4 to 24 carbon atoms, alkynylene of 4 to 24 carbon atoms, cycloalkylene of 4 to 10 carbon atoms or said radical substituted by lower alkyl, lower alkoxy, chloro, fluoro, iodo, bromo, amino, lower alkoxy, carbamoyl, sulfamoyl, lower alkylthio, perhaloalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano, or where R' is poly(alkylene oxide) of 5 to 20 carbon atoms and where said alkylene contains 2 to 5 carbon atoms or where R' is phenylene, diphenylene ether, diphenylene thioether, diphenyleneimino, diphenylene (lower) alkylene or diphenylene sulfone that is unsubstituted or substituted on the aryl moiety by 1 to 3 of lower alkyl, cycloalkyl of 3 to 8 carbon atoms, lower alkoxy, chloro, bromo, fluoro, perhaloalkyl of 1 to 12 carbon atoms, nitro, cyano, thiocyano, alkylthio of 1 to 18 carbon atoms, amino, sulfamoyl, carbamoyl or said amino, sulfamoyl or carbamoyl containing one or two substituents on the nitrogen atom selected from alkyl of 1 to 18 carbon atoms, cycloalkyl of 3 to 8 carbon atoms, aryl of 6 or 10 carbon atoms in the aryl nucleus or acyl as previously defined, and where said nitrogen substituents are further unsubstituted or substituted by chloro, fluoro, iodo, bromo, amino, lower alkoxy, carbamoyl, sulfamoyl, lower alkylthio, perfluoroalkyl of 1 to 12 carbon atoms, acyl of 2 to 5 carbon atoms, carbalkoxy of 2 to 5 carbon atoms, acylamino of 2 to 5 carbon atoms, nitrile, nitro, and thiocyano or where R' is alkylene interrupted by methylenedioxy or $C_4$ to $C_{10}$ cycloalkylene or where R' is the residue of an organic diisocyanate of formula

OCN—B—NCO where B is aliphatic, aromatic or aliphatic-aromatic, or a polyurethane prepolymer or where R' is the residue of an organic diepoxide of the formula:

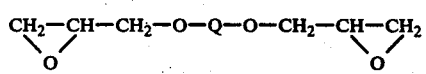

wherein Q is phenylene, diphenylene ether, diphenylene thioether, diphenyleneimino, diphenylene (lower) alkylene or diphenylene sulfone that is unsubstituted or substituted on the aryl moiety by 1 to 3 of lower alkyl, cycloalkyl of 3 to 8 carbon atoms, lower alkoxy, chloro, bromo, fluoro, perhaloalkyl of 1 to 12 carbon atoms, nitro, cyano, thiocyano, alkylthio of 1 to 18 carbon atoms, amino, sulfamoyl, carbamoyl, or said amino, sulfamoyl, or carbamoyl containing one or two substituents on the nitrogen atom selected from alkyl of 1 to 18 carbon atoms, cycloalkyl of 3 to 8 carbon atoms, aryl of 6 or 10 carbon atoms in the aryl nucleus, or acyl as previously defined, and where said nitrogen substituents are further unsubstituted or substituted by chloro, fluoro, iodo, bromo, amino, lower alkoxy, carbamoyl, sulfamoyl, lower alkyl thio, perfluoroalkyl of 1 to 12 carbon atoms, acyl of 2 to 5 carbon atoms, carbalkoxy of 2 to 5 carbon atoms, acyl amino of 2 to 5 carbon atoms, nitrile, nitro and thio cyano, or wherein Q is alkylene of 2 to 24 carbon atoms, alkenylene of 4 to 24 carbon atoms, alkynylene of 4 to 24 carbon atoms, cycloalkylene of 4 to 10 carbon atoms, or said radical substituted by lower alkyl, lower alkoxy, chloro, fluoro, iodo, bromo, amino, lower alkoxy, carbamoyl, sulfamoyl, lower alkyl thio, perhaloalkyl, of 1 to 12 carbon atoms, acyl, of 2 to 5 carbon atoms, carbalkoxy of 2 to 5 carbon atoms, acylamino, of 2 to 5 carbon atoms, nitrile, nitro, or thio cyano, and where all of $R_1$, $R_2$, $R_3$, $R_4$, $R_5$ and $R_6$ are not simultaneously hydrogen, provided however that when R is

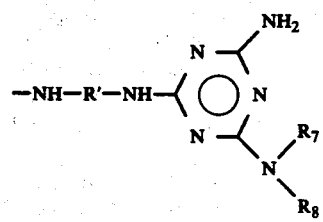

$R_1$, $R_2$, $R_7$ and $R_8$ can all be hydrogen.

In the preferred embodiment of this invention R is

or

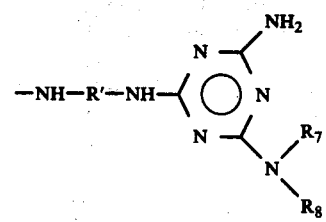

and these compounds have the formula

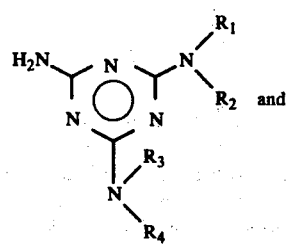

-continued

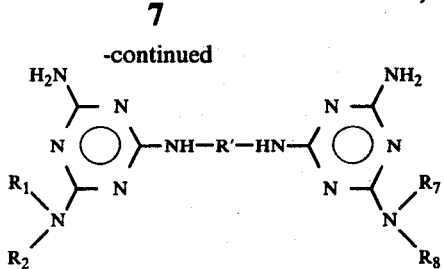

where the substituents are as previously defined.

A useful group of compounds is that represented by the above formulae in which $R_1$, $R_2$, $R_3$, $R_4$, $R_7$ and $R_8$ independently are hydrogen, alkyl of 1 to 24 carbon atoms or alkenyl chloro, bromo, carboloweralkoxy, lower alkoxy, acyl or acyloxy of 2 to 5 carbon atoms, amino, carbamoyl or sulfamoyl that are unsubstituted or substituted on the nitrogen by one or two radicals independently selected from lower alkyl, cycloalkyl of 4 to 7 carbon atoms, phenyl, acyl of 2 to 5 carbon atoms or where said nitrogen substituents together with the associated nitrogen atom from morpholinyl piperidyl or piperazyl, and where said nitrogen substituents are further unsubstituted or substituted by chloro, amino, lower alkoxy, carbamoyl, sulfamoyl, acyl, acylamino or carbalkoxy of 2 to 5 carbon atoms, nitro or nitrile cyano, phenyl or acylamino of 2 to 5 carbon atoms or where $R_1$, $R_2$, $R_3$, $R_4$, $R_7$ and $R_8$ each independently is phenyl or naphthyl that is unsubstituted or substituted by one to three of lower alkyl, lower alkoxy, chloro, bromo, nitro, cyano or amino sulfamoyl or carbamoyl that is unsubstituted or substituted on the nitrogen atom by one or two radicals selected from lower alkyl, phenyl and acyl of 2 to 5 carbon atoms, said substituents being further unsubstituted or substituted by chloro, lower alkyl, lower alkoxy, amino, carbamoyl, sulfamoyl, acyl, acylamino or carbalkoxy of 2 to 5 carbon atoms, or cyano acyl or acylamino of 2 to 5 carbon atoms, carboloweralkoxy, or where one of the pairs $R_1$-$R_2$ or $R_3$-$R_4$, or one or both of the pairs of $R_1$-$R_2$ and $R_7$-$R_8$ together with the associated nitrogen atom forms morpholinyl, piperidyl, or piperazyl, and where R' is as previously defined, and where some, but not all, of $R_1$, $R_2$, $R_3$ and $R_4$ are hydrogen.

A preferred group of compounds are those melting in the range 70° to 180° C. having the formula

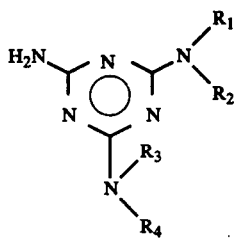

where $R_1$, $R_2$, $R_3$ and $R_4$, each independently is selected from hydrogen, alkyl of 1 to 24 carbon atoms that is unsubstituted or substituted by lower alkoxy chloro, loweralkoxycarbonyl, cyano, amino, N-loweralkylamino, N,N-diloweralkylamino, piperidyl, morpholinyl and phenyl, alkenyl of 2 to 8 carbon atoms and phenyl that is unsubstituted or substituted or substituted by chloro, bromo, nitro, lower alkyl, lower alkoxy, or lower alkoxycarbonyl or where one of the pairs $R_1$-$R_2$ and $R_3$-$R_4$ together with the associated nitrogen atom form morpholinyl or piperidyl and where all of $R_1$, $R_2$, $R_3$ and $R_4$ are not simultaneously hydrogen.

Especially preferred are the compounds where three of $R_1$, $R_2$, $R_3$ and $R_4$ are hydrogen; most especially when the remaining member is alkyl of 2 to 24 carbon atoms or said alkyl substituted by lower alkoxy.

A useful group of compounds having the formula

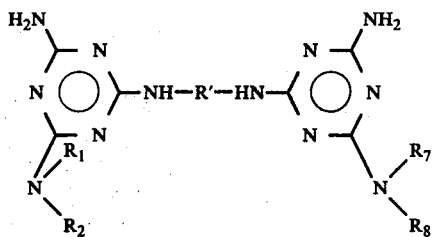

are those where $R_1$, $R_2$, $R_7$ and $R_8$ are as previously defined and R' is alkylene of 2 to 24 carbon atoms, poly(alkylene oxide), diphenylene methane, alkylene interrupted by methylenedioxy or where R' is the residue of an organic diisocyanate.

Particularly preferred are the compounds where $R_1$, $R_2$, $R_7$ and $R_8$ are hydrogen and R' is alkylene from 2 to 18 carbon atoms that may be interrupted by methylene dioxy or R' is poly(alkylene oxide) of 5 to 20 carbon atoms or where $R_1$ and $R_7$ are hydrogen, $R_2$ and $R_8$ are alkyl of 2 to 18 carbon atoms and R' is the residue of toluene diisocyanate.

The bis melamine compounds described herein generally melt above the desired range of 70° to 180° C.; however they can be blended with the lower-melting triazine compounds described to provide a mixture that melts within the desired range or they may be dissolved in the molten prepolymer. Thus bis melamines are typically present in an amount of from about 1% to about 100% based on the weight of curing agent present. The amount used is not critical, and, as can be seen from Example 6 helps to accelerate the cure without adversely affecting the physical properties of the cured product.

The term polyurethane prepolymer as used in this application is used in the same manner as in the prior art. Such polyurethane prepolymers are ususally prepared by reacting an excess of an organic diisocyanate of general formula

OCN—B—NCO where B is a divalent organic radical, with a polyether or polyester polyol having a molecular weight of about 400 to 10,000, usually 600 to 7,000 and preferably 1,000 to 6,000 so that the prepolymer is NCO terminated. The equivalent ratio of diisocyanate to polyol should be greater than one and is preferably large enough so that the polyurethane prepolymer melts below 80° C. and preferably is liquid at room temperature.

Among the reactive organic polyfunctional polyols employed in preparing the polyurethane prepolymers used in the practice of the invention by reaction with a suitable isocyanate compound are the polyalkylene ether, thioether, and ether-thioether glycols represented by the general formula:

$$HO-(RX)_n-H$$

wherein R represents the same or different alkylene radicals containing up to about 10 carbon atoms, X represents oxygen or sulfur, and n is an integer large enough so that the molecular weight of the polyalkylene ether, thioether, or ether-thioether glycol is at least about 400, e.g., from about 400 to about 10,000. The polyalkylene ether glycols included within this general formula, such as polyethylene glycols, polypropylene glycols, polybutylene glycols, polytetramethylene glycols, polyhexamethylene glycols, and the like, which are obtained, for example, by acid-catalyzed condensation of the corresponding monomeric glycols or by the condensation of lower alkylene oxides, such as ethylene oxide, propylene oxide, and the like, either with themselves or with glycols such as ethylene glycol, propylene glycol, and the like are preferred.

Polyalkylenearylene ether, thioether and ether-thioether glycols which also have molecular weights ranging from about 400 to about 10,000 but which differ from the above-described polyalkylene glycols in having arylene radicals, such as phenylene, naphthylene and arylene radicals, either unsubstituted or substituted, e.g., with alkyl or aryl groups, and the like, in place of some of the alkylene radicals of said polyalkylene glycols may also be employed as polyol reactants. Polyalkylenearylene glycols of the type ordinarily used for this purpose will usually contain at least one alkylene ether radical having a molecular weight of about 500 for each arylene radical present.

Essentially linear polyesters containing a plurality of isocyanate-reactive hydroxyl groups constitute another class of reactive organic polyfunctional polyols which may be employed in preparing polyurethane useful in the practice of the present invention. While the preparation of polyesters suitable for this purpose has been described in great detail in the prior art, and forms no part of the present invention per se, it may be mentioned here by way of illustration that polyesters of this type may be prepared by the condensation of a polyhydric alcohol, generally a saturated aliphatic diol such as ethylene glycol, propanediol-1,2, propanediol-1,3, butanediol-1,3, butanediol-1,4 pentanediol-1,2, pentanediol-1,5, hexanediol-1,3, hexanediol-1,6 diethylene glycol dipropylene glycol, triethylene glycol, tetraethylene glycol, and the like, as well as mixtures of such diols with each other and with minor amounts of polyols having more than two hydroxyl groups, preferably saturated aliphatic polyols such as glycerol, trimethylol ethane, trimethylol propane, pentaerythritol, sorbitol, and the like, with a polycarboxylic acid or anhydride, generally a dicarboxylic acid or anhydride which is either saturated or which contains only benzenoid unsaturation, such as oxalic, malonic, succinic, glutaric, adipic, pimelic, suberic, azelaic, sebacic, malic, phthalic, cyclohexanedicarboxylic, and endomethylenetetrahydrophthalic acids, and the like and their isomers, homologs, and other substituted derivatives, e.g. chloroderivatives, or with mixtures of such acids with each other and with unsaturated dicarboxylic acids or anhydrides such as maleic, fumaric, citraconic, and itaconic acids, and the like, as well as with polycarboxylic acids containing three or more carboxyl groups such as aconitic acid and the like.

The essentially linear polyesters commonly used in preparing polyurethane resins preferably have molecular weights ranging from about 750 to about 3,000. In addition, they will generally have relatively low acid numbers, e.g., acid numbers not appreciably in excess of about 60 and preferably as low as can be practicably obtained, e.g., 2 or less. Correspondingly, they will generally have relatively high hydroxy numbers, e.g., from about 30 to about 700. When preparing these polyesters, an excess of polyol over polycarboxylic acid is generally used to insure that the resulting essentially linear polyester chains contain a sufficient amount of reactive hydroxyl groups.

Another class of suitable organic polyfunctional polyol reactants includes polyalkylene ether polyols containing more than two reactive hydroxyl groups such as polyalkylene ether triols, tetrols, and the like, which are prepared, for example, by reacting polyols such as glycerol, trimethylol ethane, trimethylol propane, pentaerythritol, dipentaerythritol, sorbitol, and the like, with lower alkylene oxides such as ethylene oxide, propylene oxide, and the like.

Nitrogen-containing polyfunctional polyols may also be used as polyol reactants. Among such materials there are included the polyesteramides conventionally employed in the preparation of polyurethane resins, i.e. those having molecular weights ranging from about 750 to about 3,000, acid numbers ranging from about 60 as a maximum to as low as can be practicably obtained, e.g. 2 or less, and hydroxyl numbers ranging from about 30 to about 700, and also high molecular weight polyamino alcohols, such as hydroxypropylated alkylene diamines of the general formula $$(HOH_6C_3)_2N-R_a-N(C_3H_6OH)_2$$

wherein $R_a$ represents an alkylene radical having from 2 to 6 carbon atoms, inclusive of which, N,N,N',N'-tetrakis-(2-hydroxypropyl)-ethylenediamine is a representative species, as well as higher analogs thereof, such as hydroxypropylated polyalkylenepolyamines of the general formula $$(HOH_6C_3)_2N-R_a-N-R_a-N(C_3H_6OH)_2$$
$$\phantom{(HOH_6C_3)_2N-R_a-N-R_a-}|$$
$$\phantom{(HOH_6C_3)_2N-R_a-N-R_a-}C_3H_6OH$$

wherein $R_a$ is as defined hereinabove (see U.S. Pat. No. 2,697,118 to Lundsted et al.).

As can be readily appreciated, mixtures of the various reactive organic polyfunctional polyols described hereinabove may also be employed in preparing polyurethane prepolymers useful in the practice of the present invention.

The polyester or polyether polyol as described above can be combined with a slight excess of any of a large number of polyisocyanates to form the polyurethane prepolymer. As previously indicated the polyisocyanate can conveniently be represented by the formula $$OCN-B-NCO$$

where B is a divalent organic radical and can be aliphatic, aromatic or aliphaticaromatic. Thus, divalent radical B can be phenylene that is unsubstituted or substituted by chloro, nitro, lower alkoxy, lower alkyl, phenoxy and phenyl diphenylene that is unsubstituted or substituted by lower alkyl or lower alkoxy, biphenylene (lower) alkylene that is unsubstituted or substituted by lower alkoxy, halogen alkylene of 2 to 8 carbon atoms that is unsubstituted or substituted by lower alkoxy cycloalkylene of 4 to 8 carbon atoms that is unsubstituted or substituted by lower alkyl and bis cyclohexylene (lower) alkylene.

Divalent organic radical, B as is seen, can be substituted by various substituents such as, for example, halogen, notably chlorine, bromine, fluorine and iodine, nitro lower alkoxy, lower alkyl, phenyl and phenoxy. Representative polyisocyanates include:

1-chlorophenyl-2,4-diisocyanate,
1-nitrophenyl-2,4-diisocyanate,
1,3-dichlorophenyl-4,6-diisocyanate,
1,4-dichlorophenyl-2,5-diisocyanate,
1-chloro-4-methoxyphenyl-2,5-diisocyanate,
1-methoxyphenyl-2,4-diisocyanate,
1-methyl-4-methoxyphenyl-2,5-diisocyanate
1-ethoxyphenyl-2,4-diisocyanate,
1,3-dimethoxyphenyl-4,6-diisocyanate,
1,4-dimethoxyphenyl-2,5-diisocyanate,
1-propoxyphenyl-2,4-diisocyanate,
1-isobutoxyphenyl-2,4-diisocyanate,
1,4-diethoxyphenyl-2,5-diisocyanate,
toluene-2,4-diisocyanate,
toluene-2,6-diisocyanate,
diphenylether-2,4-diisocyanate,
naphthalene-1,4-diisocyanate,
1,1'-dinaphthalene-2,2'diisocyanate,
biphenyl-2,4-diisocyanate
3,3'-dimethylbiphenyl-4,4'diisocyanate,
3,3'-dimethoxybiphenyl-4,4'-diisocyanate,
diphenylmethane-4,4'-diisocyanate,
diphenylmethane-2,4'-diisocyanate,
diphenylmethane-2,2'-diisocyanate,
3,3'-dimethoxydiphenylmethane-4,4'-diisocyanate,
3,3'-dichlorodiphenyldimethylmethane-4,4'-diisocyanate,
benzophenone,-3,3'-diisocyanate,
ethylene diisocyanate,
propylene diisocyanate,
butylene diisocyanate,
pentylene diisocyanate,
methylbutylene diisocyanate,
tetramethylene diisocyanate,
pentamethylene diisocyanate,
hexamethylene diisocyanate,
dipropyldiisocyanate ether,
heptamethylene diisocyanate,
2,2-dimethylpentylene diisocyanate,
3-methoxy-hexamethylene diisocyanate,
octamethylene diisocyanate,
2,2,4-trimethylpentylene diisocyanate,
3-butoxyhexamethylene diisocyanate,
1,3-dimethyl benzene diisocyanate,
1,4-dimethyl benzene diisocyanate,
1,2-dimethylcyclohexane diisocyanate,
1,4-dimethylcyclohexane diisocyanate,
1,4-diethylbenzene diisocyanate,
1,4-dimethylnaphthalene diisocyanate,
1,5-dimethylnaphthalene diisocyanate,
cyclohexane-1,3-diisocyanate,
cyclohexane-1,4-diisocyanate,
1-methylcyclohexane-2,4-diisocyanate,
1-methylcyclohexane-2,5-diisocyanate,
1-ethylcyclohexane-2,4-diisocyanate,
dicyclohexylmethane-4,4'-diisocyanate,
dicyclohexylmethylmethane-4,4'-diisocyanate,
dicyclohexyldimethylmethane-4,4'-diisocyanate,
2,2-dimethyldicyclohexylmethane-4,4'-diisocyanate,
3,3',5,5'-tetramethyldicyclohexylmethane-4,4'-diisocyanate,
3-nitrotriphenylmethane-4,4'-diisocyanate,
pyrene-3,8-diisocyanate,
chrysene-2,8-diisocyanate,
4,4'-methylenebis(cyclohexylisocyanate); ethylidine diisocyanate; propylene-1,2-diisocyanate; 4,4'-diphenyl diisocyanate; dianisidine diisocyanate; 1,5-naphthalene diisocyanate; 4,4'-diphenyl ether diisocyanate; m- and p-phenylene diisocyanate; 4,4'-toluidene diisocyanate; isopropylidene bis[phenyl or cyclohexyl isocyanate]; 1,3-cyclopentylene diisocyanate; 1,2-cyclohexylene diisocyanate; 1,4-cyclohexylene diisocyanate; chloro diphenyl diisocyanate; 4,4',4"-triphenyl methane triisocyanate; 1,3,5-triisocyanate benzene; phenylethylene diisocyanate.

In the process of the invention, it is desirable to maintain homogeneity with the reactants from the time when they are mixed to the time when they have completely reacted to form the final cured polymer. Generally, when a fluid isocyanate terminated polyurethane prepolymer prepared, for example, by reacting an excess of an organic isocyanate with a polyester polyol, is cured by the process of this invention, the substituted di- or triamino-s-triazine curing agent is added to the fluid isocyanate terminated polyurethane prepolymer and the resulting admixture is heated to a temperature of about 80° C. to about 180° C. over a reaction time ranging from about 0.5 to about 30 hours. The preferred cure time in from about 0.5 to about 20 hours and the typical cure temperature is from about 90° C. to about 150° C.

The quantity of di- or triamino-s-triazine curing agent utilized in preparing cured polyurethane polymers can be varied over a wide stoichiometric range. In making such computations it has been found useful to assume that the di- and triamino-s-triazines described herein have a functionality of 2 and that the biscompounds have a functionality of 4. The stoichiometry employed can range from 70 to 140%. It will be obvious to a chemist skilled in the urethane art that the selection of a particular stoichiometric ratio within this range will depend on the particular properties which are desired in the cured product, as well as, to some degree, the cure speed desired.

Because of the reactivity of the di- or triamino-s-triazine curing agent and the polyurethane prepolymer, cure takes place without the aid of catalysts. Conventional curing catalysts may be employed, if desired, but in most cases their use will not appreciably spped the cure rate. If very fast cure is desired, the polyurethane product may be heated, for example, in an oven at a temperature up to about 250° F. to 300° F. until a full cure is attained. Inasmuch as the time required for full cure is generally inversely related to the temperature of cure and depend on other factors such as the particular prepolymer used, the degree of cure desired, the size of the article, the character of the heating device etc., it is to be understood that curing conditions are not critical but simply follow conventional practice. As is known in the art, the physical properties of the cured polyurethanes may in some instances be optimized by heat aging the cured polyurethane at temperatures between about 25° and 130° C. for periods of time ranging from hours to several days.

It will be apparent that, in addition to using the di- and triamino-s-triazines, bismelamines and mixtures thereof as curing agents, other active hydrogen compounds, such as, the polyols listed herein above may be used as co-curing agents with them. The techniques involving the incorporation of these co-curatives with the curing agents of the present invention will be analogous to those described herein for cures without co-curatives, and will be readily employable by one skilled in the art.

In general, the polyurethane polymers cured according to this invention are susceptible to the same processing techniques as polyurethane polymers produced by the use of conventional curing agents.

The di- and triamino-s-triazines useful herein can be prepared by a variety of synthetic techniques.

According to one technique, melamine can be reacted with an amine or amine hydrochloride at a temperature range of 150° to 200° either with or without solvent to provide substituted melamines as products. The general reaction is illustrated below.

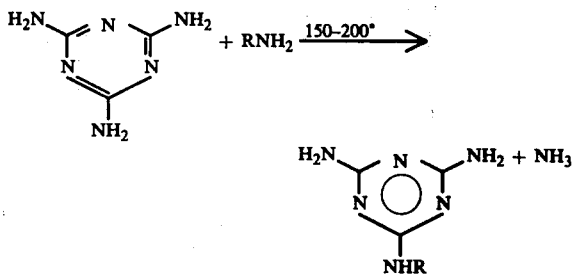

cf German Patent No. 889,593 (1953)

The most widely applicable and most convenient synthetic method for substituted melamines is that based on the reaction of cyanuric chloride (or cyanuric bromide) or a chloroamino-s-triazine with ammonia or an amine. This approach, which was first used by Hoffman in 1885 allows the preparation of mono-di-trisubstituted melamines, symetrically or asymetrically substituted.

N-substituted melamines have also been prepared by the reaction of substituted cyanamides with cyanoguanidine according to the following general formula.

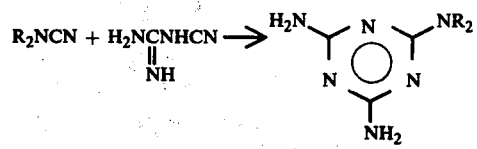

Substituted melamines can also be prepared by replacement of groups other than chlorine atoms on the s-triazine ring. Thus, alkyl thio groups on cyanuric thioesters can be replaced by a means according to the following formula.

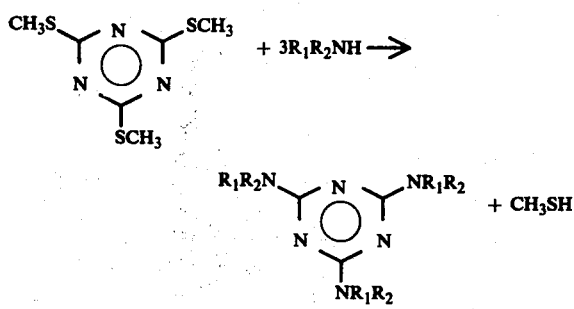

Similarly, one can heat thioammeline with an amine to obtain a substituted melamine.

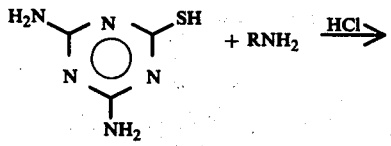

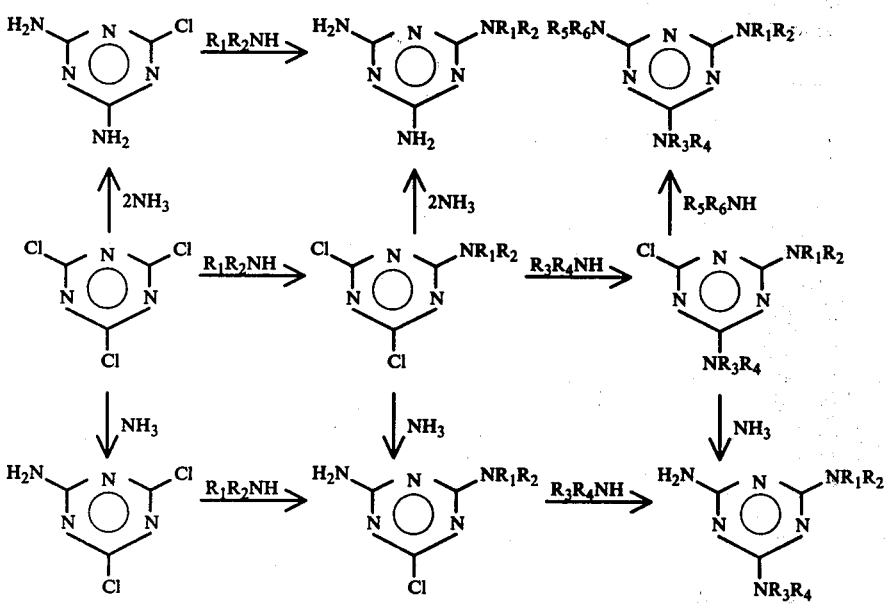

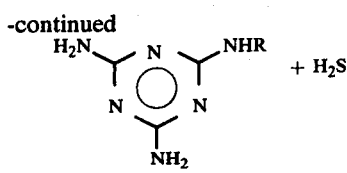 + $H_2S$

In like manner, the aryloxy-s-triazines can be reacted with amines to prepare certain substituted melamines difficult to isolate by the cyanuric chloride route.

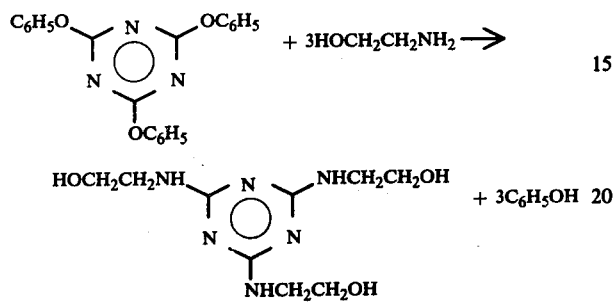

It is also possible to replace the hydroxyl groups of ammeline, ammelide and cyanuric acid with amines to yield mono di and tri-substituted melamines, at temperatures of 350° C. under pressure according to the following formula.

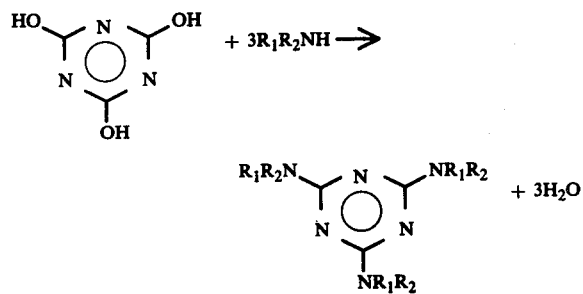

The reaction of amines with cyanoguanidine at temperatures of 120° to 250° C. can lead to substituted melamines.

Further, it is possible to react 1,3-di-cyanoguanidine with an amine under strongly acidic conditions to obtain good yields of N-substituted melamines according to the following equation.

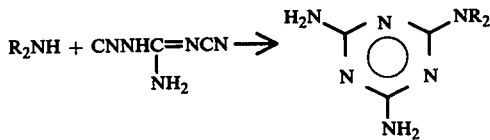

One knowledgeable in organic chemistry will recognize that di and triamino-as-triazines analogous to the s-triazines of the instant invention may be prepared by well known synthetic methods. as-Triazine analogs of the bismelamines may also be prepared. The compounds so formed can be used as curatives for isocyanate terminated prepolymers, and are thus equivalents, for this purpose, of the s-triazines and bis-melamines described herein.

EXAMPLE 1

This example illustrates the synthesis of substituted di- and tri-amino-s-triazines.

A. Conversion of cyanuric chloride to 2,4-diamino-6-chloro-s-triazine

Cyanuric chloride (368.8 grams, 2 mole) was dissolved in 800 mls of hot actone, After removal of the insoluble portion by filtration, the hot solution was added to eight moles of ammonia dissolved in 2000 mls of water. An ice bath was used to keep the reaction temperature below 50° C. After completion of addition, the reaction was heated 4 hours at 40°-45° C.

The product was recovered by filtration and washed thoroughly with cold water. After drying in a vacuum oven at 60°-70° C. the yield amounted to 90% of theory. The compound is an infusible white solid.

Calculated: 24.63% Cl: Found: 25.74% Cl.

B. Preparation of Octadecyl Melamine 2,6-Diamino-4-chloro-s-triazine (100 g., 0.7 mole), octadecyl amine (207 g., 0.7 mole), and sodium carbonate (100 g) were dissolved in 1000 mls of dimethyl formamide and heated at 100° C. for 4 hours. While still hot, the contents of the reactor was filtered to remove the inorganic salts. When the hot filtrate was allowed to cool, the crude octadecyl melamine precipitated. With filtration, 208 grams (M.P. 78°-82° C.) of a pale yellow solid was recovered. Addition of the second filtrate to cold water yielded an additional 48 grams of solid (M.P. 60°-80° C.).

After recrystallization from dioxane, and then ethyl acetate, 114 grams of a pale white solid, M.P. 95°-97° C., was isolated. Further recrystallization did not sharpen the melting point. The compound was characterized by IR and the following elemental analysis.

Calculated for $C_{21}H_{42}N_6$: C 66.62, H 11.18, N 22.19 Found: C 69.53, H 11.85, N 19.50: % Yield (Recrystallized Product) 43%.

C. Preparation of n-Hexylmelamine

A mixture of 72.8 g. (0.500 mole) of 2,4-diamino-6-chloro-s-triazine, 63.6 g. (0.600 mole) of anhydrous sodium carbonate, and 200 ml. of N,N-dimethylformamide (DMF) was heated over 43 minutes of 124° C. To this was added, over a period of 2.35 hours, a solution of 60.7 g. (0.600 mole) of n-hexylamine in 100 ml. of DMF; temperature was controlled at 122°-127° C. during the addition. The reaction mixture was heated for an additional 19 hours at 124°-125° C., then was filtered hot. The filter cake was washed with 100 ml of hot DMF, and the combined filtrate was cooled and added with stirring to about 5 liters of ice-water. The precipitate was recovered by filtration, reslurried with 3 liters of water, filtered again, washed thoroughly with deionized water, and dried to constant weight in a vacuum oven at 60° C. The yield of n-hexylmelamine, m.p. 115°-117.5° C., was 91.4 g. (87.0%).

D. Preparation of (3-methoxypropyl) Melamine (3-methoxypropyl) melamine was prepared by using 3-methoxypropylamine in place of n-hexylamine in part C above. The product was isolated as the hydrochloride, m.p. 204° C.

Anal. Calcd. for $C_7H_{15}ClN_6O$: C, 35.82; H, 6.44; N, 35.81; Cl, 15.11. Found: C, 36.24; H, 6.50; N, 35.30; Cl, 15.13.

It was converted to the free amine, m.p. ca 160° C., by treatment with sodium hydroxide and sodium chloride in water.

Anal. Calcd. for $C_7H_{14}N_6O$: C, 42.41; H, 7.12; N, 42.40. Found: C, 42.26; H, 7.34; N, 41.98.

Comparable results are obtained using bis(2-aminoethyl) formal of formula

as indicated in the table.

TABLE

| | | Bis(melamines) | | | Analyses (2) | | |
|---|---|---|---|---|---|---|---|
| R' | DMF (1) | Yield, % | Melt. Pt. Approx., C | Formula | C | H | N |
| $(CH_2)_6$ | 1 | 85.0 | 291 | $C_{15}H_{29}N_{13}O$ | (44.21) 43.48 | (7.17) 7.38 | (44.69) 46.13 |
| $(CH_2)_3OCH_2CH_2OCH_2CH_2O(CH_2)_3$ | 0 | 88.3 | 255 | $C_{16}H_{30}N_{12}O_3$ | (43.83) 44.27 | (6.90) 6.93 | (38.33) 37.74 |
| $(CH_2)_{12}$ | 1 | 88.1 | 110 | $C_{21}H_{41}N_{13}O$ | (51.30) 51.04 | (8.41) 8.61 | (37.04) 36.27 |
| $CH_2CH_2OCH_2OCH_2CH_2$ | 1 | 62.8 | 202 | $C_{14}H_{27}N_{13}O$ | (39.52) 38.38 | (6.40) 6.83 | (42.80) 43.03 |
| trimethyl hexyl (See Note 3) | 0 | 97.6 | 269 | $C_{15}H_{28}N_{12}$ | (47.86) 48.08 | (7.50) 7.11 | (44.65) 43.28 |

(1) Number of moles of DMF apparently present per mole of crystals
(2) In each entry the theoretical values are given in parentheses.

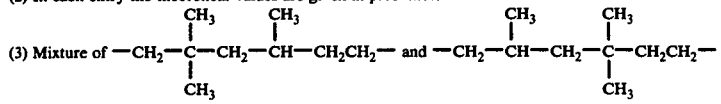

E. Preparation of Bis(melamines)

Bis (Melamines) of general formula

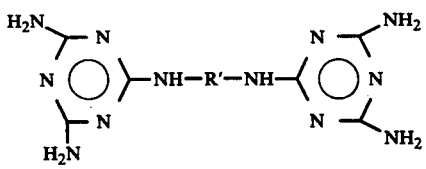

were prepared from 2,4-diamino-6-chloro-s-triazine and a diamine, $H_2N$-$R'$-$NH_2$ where the radical $R'$ corresponds to the table below, using the procedure of part C above. Some of these compounds appeared, on the basis of elemental analyses, to be the solvates, containing one mole of solvent (DMF) per mole of bis(melamine).

F. The procedure of part C above was used to prepare the bis(melamine) of formula

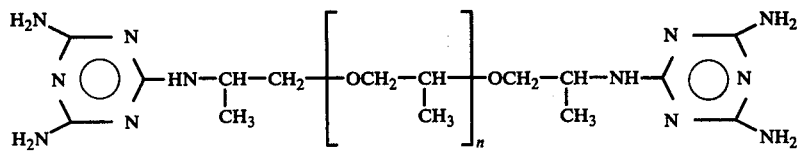

from 2,4-diamino-6-chloro-s-triazine and a diamine mixture sold under the tradename Jeffamine D-230 by Jefferson Chemical Company, Inc., Austin, Texas, and having the approximate average composition

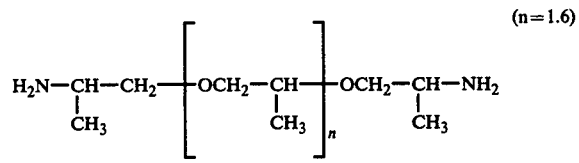

The product, obtained in a 70% yield, melted at about 107° C.

Anal. Calcd. for $C_{16.8}H_{31.6}N_{12}O_{2.6}$: C, 45.52; H, 7.19; N, 37.91. Found: C, 44.99; H, 8.43; N, 35.55.

It is apparent that by selecting an appropriate diamine R' can be varied at will. Thus, to obtain an alkylene group one can use 1,3-diaminopropane, 1,4-diaminobutane, 1,5-diaminopentane, 1,7-diaminoheptane, 1,10-diaminodecane, 1,12-diaminododecane, alkenylene is obtained by such diamines as 1,4-diaminobutene-2, 1,7-diaminoheptene-3, 1,8-diaminooctene-4, alkynylene is obtained from such compounds as 1,7-diaminoheptyne-3, cycloalkylene is obtained from such compounds as 1,2-diaminocyclohexane, arylene is obtained from such compounds as p-phenylenediamine, diaminotoluene, diaminoxylene, diaminodiphenylamine, diaminodiphenylsulfone, diaminodiphenylmethane, diaminodiphenyl thioether and diaminodiphenylether. The poly-(alkylene oxide) can be obtained from the diamine of well-known polyalkylene glycols, as illustrated.

Alkylene interrupted by methylenedioxy is obtained from bis(2-aminoethyl) formal.

EXAMPLE 2

A. An NCO-terminated prepolymer was obtained by condensing a mixture of ethylene and propylene glycols (80/20 ethylene/propylene) with adipic acid to obtain a polyester polyol, molecular weight about 2500, and thereafter reacting the polyol with toluene diisocyanate (80% 2,4-isomer and 20% 2,6-isomer) to provide an NCO-terminated polyurethane prepolymer having an NCO content of 3-4%.

B. An isocyanate-terminated polyurethane prepolymer prepared as in part A above was cured with octadecylmelamine and the product compared with the same composition cured with 4,4'-methylenebis (2-chloroaniline):

To 100 parts of molten prepolymer were added the indicated amounts of the indicated ingredient and the mixture cured for 16 hours in a closed mold at 100° C.

| INGREDIENT | A | B | C | D |
|---|---|---|---|---|
| Prepolymer | 100 | 100 | 100 | 100 |
| Octadecylmelamine | 14 | 16 | 10.8 | — |
| Triethylenediamine | 0.5 | 0.5 | 0.5 | — |
| 4,4'-methylene bis (2-chloroaniline) | — | — | — | 10 |

The cured compositions displayed the following physical properties

| INGREDIENT | A | B | C | D |
|---|---|---|---|---|
| Tensile, psi | 6340 | 6366 | 5174 | 6150 |
| Elongation % | 640 | 700 | 590 | 740 |
| Shore A/D | 73/22 | 73/22 | 65/18 | 78/ |
| 100% Mod. | 475 | 460 | 360 | 500 |
| 200% Mod. | 690 | 680 | 540 | 630 |
| 300% Mod. | 970 | 850 | 730 | 880 |
| 400% Mod. | 1600 | 1330 | 1400 | 1400 |
| 500% Mod. | 3100 | 2340 | 2800 | 2410 |
| Tear (Die c) | 413 | 316 | 309 | 345 |

With the exception of a slightly lower hardness, the physical properties of the urethanes cured with octadecylmelamine were very similar to the 4,4'-methylenebis (2-chloroaniline) cure - particularly formulation B.

EXAMPLE 3

A polyester polyol prepared from ethylene glycol and adipic acid was reacted with excess toluene diisocyanate (100% 2,4-isomer) to provide a polyurethane prepolymer having an NCO content of about 4.5%.

The effect of cure stoichiometry on the physical properties of this prepolymer cured with n-hexylmelamine and 4,4'-methylenebis (2-chloroaniline) was evaluated by combining molten prepolymer with the indicated amount of curing agent and curing the composition as indicated.

| Curing Agent | 4,4'-methylenebis (2-chloroaniline) | | | n-HEXYLMELAMINE | | | | |
|---|---|---|---|---|---|---|---|---|
| Stoichiometry, % | 85 | 90 | 105 | 75 | 85 | 95 | 100 | 105 |
| Equiv. NCO/NH$_2$ | 1.18 | 1.05 | 0.95 | 1.33 | 1.18 | 1.05 | 1.00 | 0.95 |
| g Curative/100 g Resin | 11.7 | 13.1 | 14.5 | 8.1 | 9.2 | 10.2 | 10.8 | 11.3 |
| Cure Conditions | | | | | | | | |
| Pot life at 212° F, min. | 7–8 | 7–8 | 6–7 | — | 14–15 | 13–14 | — | 13–14 |
| Cure Time at 212° F | ½hr | ½hr | ½hr | 16hrs. | 16hrs. | 16hrs. | 16hrs. | 16hrs. |
| Post Cure at 212° F | 16hrs. | 16hrs. | 16hrs. | None | None | None | None | None |
| Physical Properties (after 2 weeks at R.T.) | | | | | | | | |
| Tensile, psi | 5560 | 7280 | 4900 | 6750 | 7260 | 6920 | 7480 | 6345 |
| Elongation, % | 470 | 525 | 640 | 590 | 590 | 630 | 670 | 740 |
| Hardness, Shore A | 89 | 90 | 90 | 80 | 84 | 85 | 85 | 86 |
| Modulus, psi | | | | | | | | |
| 100% | 980 | 980 | 880 | 1000 | 1000 | 1010 | 1000 | 1000 |
| 200% | 1300 | 1300 | 1070 | 1450 | 1450 | 1400 | 1410 | 1310 |
| 300% | 1990 | 1910 | 1450 | 2080 | 2010 | 1950 | 1900 | 1650 |
| 400% | 3650 | 3300 | 2100 | 3070 | 2970 | 2780 | 2670 | 2225 |
| 500% | — | 6150 | 2960 | 4950 | 5070 | 4190 | 3800 | 3050 |
| Tear, Die C, pli | 540 | 585 | 545 | 675 | 620 | 655 | 715 | 670 |

It is seen that the results obtained with n-hexylmelamine compare favorably with the 4,4'-methylenebis (2-chloroaniline) cure; the n-hexylmelamine additionally provides a longer pot life.

A cured product is also obtained when an isocyanate-terminated polyol as described above is cured with a substituted triamino-s-triazine having the indicated formula and melting point:

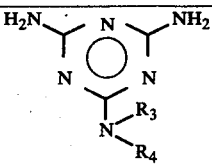

| R$_3$ | R$_4$ | MP° C |
|---|---|---|
| H | C$_2$H$_5$ | 171-2 |
| H | n-C$_4$H$_9$ | 167-9 |
| H | iso-C$_4$H$_9$ | 160-6 |
| H | t-C$_4$H$_9$ | 156-8 |
| H | $-\overset{\underset{\displaystyle CH_3}{\displaystyle CH_3}}{\underset{}{C}}-CH_2-C(CH_3)_3$ | 160-2 |
| H | C$_12$H$_25$ | 110 |
| H | CH$_2$CH$_2$CH$_2$N(C$_2$H$_5$)$_2$ | 132 |
| H | CH$_2$CH$_2$CH$_2$N(CH$_2$CH$_2$)$_2$CH$_2$ (piperidine) | 152.5-3.5 |
| H | CH$_2$CH$_2$CH$_2$N(CH$_2$CH$_2$)$_2$O (morpholine) | 163-4 |

-continued

| | | | | |
|---|---|---|---|---|
| H | | 3-Cl-C6H4 | | 173–5 |
| H | | 3-NO2-C6H4 | | 144–5 |
| C2H5 | | C2H5 | | 168–70 |
| C4H9 | | C4H9 | | 134–5 |
| CH2CH=CH2 | | CH2—CH=CH2 | | 144–5 |

$$\text{triazine with } H_2N\text{-, } NR_1R_2\text{, } NR_3R_4 \text{ substituents}$$

| R1 | R2 | R3 | R4 | MP° C |
|---|---|---|---|---|
| H | C2H5 | H | C2H5 | 156–8 |
| H | C17H35 | H | C17H35 | 72–5 |
| H | CH2CH2CH2—N⎯H⟩ | H | CH2CH2CH2—N⎯H⟩ | 78–80 |
| H | CH3 | H | C2H5 | 176 |
| H | CH3 | H | C6H5 | 84–6 |
| H | C2H5 | H | C6H5 | 153–5 |
| H | iso-C3H7 | H | 4-Cl-C6H4 | 166 |
| H | CH2—C(CH3)=CH2 | H | 4-CH3-C6H4 | 137–9 |
| H | CH2CH2OH | H | C6H5 | 156–8 |
| H | CH2CH2OH | H | 4-Cl-C6H4 | 147–50 |
| H | CH2CH2OH | H | 4-Cl-C6H4 | 173–74 |
| H | CH3CH(OH)—CH2 | H | C6H5 | 138–40 |
| H | CH2CH2N(C2H5)2 | H | C6H5 | 128–9 |
| H | CH2CH2N(C2H5)2 | H | 4-Cl-C6H4 | 136–7 |

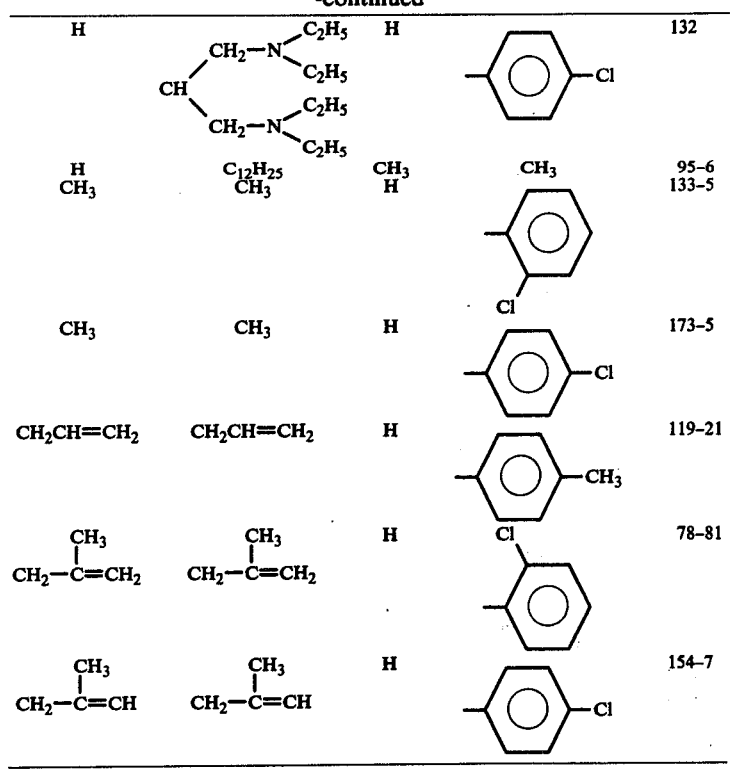

EXAMPLE 4

This Example illustrates the use of conventional amine chain-lengthening agents in conjunction with the substituted di and triamino-s-triazines of this invention.

A. To 100 grams of a molten TDI-capped polyethyleneadipate prepolymer having 4.45% NCO, were added 9.5 grams molten n-hexylmelamine and 1.0 grams of a polymeric methylenedianiline, (f = 2.3) obtained by condensing aniline with formaldehyde and sold as Curithane 103 by Upjohn and Company, at 212° F. The formulation was poured into a pre-heated 6" × 6" mold, brought to the gel-point in 10 minutes at 250°, and compression-molded 1 hour at 250° F. A sheet having excellent hot dimensional stability was obtained. Following post-cure 16 hrs/212°, and a 2 week aging period at room temperature, the following properties were measured,

| Tensile, | Elong., | Modulus, 100% | Tear, psi 300% | die C | Hardness |
|---|---|---|---|---|---|
| psi 6165 | % 485 | 935 | 2270 | pli 505 | Shore A 80 |

B. To 100 grams of a molten TDI-capped prepolymer of polyethylene adipate having 4.32% NCO were added 10.1 grams molten n-hexylmelamine and 1.0 grams molten methylene dianiline (MDA) at 212° F. The formulation was poured into a pre-heated mold and brought to the gel-point in 20 minutes at 212° F. Following compression-molding 16 hrs/212° F., the sheet was aged at room temperature for two weeks. The following properties were then measured,

| Tensile, | Elong., | Modulus, 100% | Tear, psi 300% | die C | Hardness |
|---|---|---|---|---|---|
| psi 3100 | % 430 | 900 | 1750 | pli 497 | Shore A 83 |

Other difunctional chain lengthening agents that can be used with the curing agents of this invention include, either individually or as mixtures, water, ethylene glycol, propylene glycol, butane diol-(1,4), hexane-diol-(1,6), hydroquinone-bis-hydroxyethylether, p-xylene glycol, and diamines such as ethylene diamine, 1,2-propylene diamine, 1,3-propylene diamine, 1,4-tetramethylene diamine, 1,6-hexamethylene diamine, 2,2,4-trimethylhexane diamine-(1,6), 1-methyl-cyclohexane-2,4-diamine, 1-amino-3-aminomethyl-3,5,5-trimethylcyclohexane (isophorone diamine), 4,4'-diaminodicyclohexylmethane, bis-(aminopropyl) piperazine, or aromatic diprimary amines such as 4,4'-diamino-diphenylmethane, as illustrated in part B above, 4,4'-diamino-diphenylsulphide, 4,4'-diamino-diphenylether, 1-methyl-2,4-diaminobenzene or aralphatic diprimary diamines such as m-xylylene diamine, p-xylylene diamine, 1,3-bis-(-aminoisopropyl)-benzene, or amino alcohols such as ethanol amine and the like, and hydrazides such as carbodihydrazide, oxalic acid dihydrazide, malonic acid dihydrazide, succinic acid dihydrazide, adipic acid dihydrazide, sebacic acid dihydrazide, and oxydipropionic acid dihydrazide, hydroquinone diacetic acid dihydrazide, N,N'-piperazine-bis-(propionic acid hydrazide), isophthalic acid dihydrazide, m- and p-cyclohexane dicarboxylic acid hydrazide (cis/trans), hexamethylene-bis-semicarbazide, aminoacetic acid hydrazide, and in addition, hydrazine, e.g. also in the form of hydrazine hydrate, as well as dihydrazines such as N,N'-diaminopiperazine.

EXAMPLE 5

100 grams of a molten prepolymer of polyethylene-propylene adipate capped with bis [4-isocyanate phenyl] methane (MDI), and having 5.7% NCO, was conditioned for 30 minutes at 250° F. and then combined with 24.0 grams molten n-octadecylmelamine. Reaction at 250° F. was rapid, with a work life of 2 minutes. The formulation was compression-molded in a 6″ × 6″ pre-heated mold at 300° F. for 30 minutes and post-cured 16 hrs/212° F. A homogeneous, semi-transparent amber-colored sheet was obtained, having the following properties,

| Tensile, | Elong., | Modulus, | | psi | Tear, Die C | Duro |
|---|---|---|---|---|---|---|
| psi | % | 100% | 200% | 300% | pli | Shore A |
| 1680 | 315 | 735 | 1025 | 1455 | 357 | 86 |

It should be noted in connection with this Example that it is unusual to cure an MDI-terminated prepolymer with an amine. The extreme reactivity of these prepolymers precludes obtaining a useful product with conventional amines and so diols and polyols are normally used as the curing agents.

EXAMPLE 6

This Example illustrates the use of a bismelamine in conjunction with the substituted di and triamino-s-triazines described herein to provide faster cure times than those obtained with the substituted triazines alone.

A. To 100 grams of a molten TDI-terminated prepolymer of polyethylene adipate, having 4.4% NCO, were added 9.5 grams of n-hexylmelamine and 0.8 grams of hexamethylene bismelamine at 212° F. The formulation was poured into a preheated 6″ × 6″ mold, where it reached the gel-point in 40 minutes at 212° F. Following cure for 1 hour at 240°; a transparent, colorless sheet was obtained which was post-cured 16 hours at 212°. Physical properties of the sheet are as follows,

| Tensile, | Elong., | Modulus, | | psi | Tear, Die C | Hardness |
|---|---|---|---|---|---|---|
| psi | % | 100% | 300% | 500% | pli | Shore A |
| 7065 | 565 | 995 | 2165 | 5435 | 605 | 80 |

B. 100 grams of a molten prepolymer prepared from polyethylene adipate and tolylene diisocyanate, and having 4.37% NCO, were combined with 3.9 grams of the bismelamine according to Example 1F and 6.8 grams of n-hexylmelamine at 212° F. The formulation was poured into a pre-heated 6″ × 6″ mold and compression-molded 1 hour at 240° F. following a gel-time of 14 minutes at 240° F. A transparent, colorless sheet with excellent hot dimensional stability was obtained. Following post-cure 16 hrs. at 212° F., the following physical properties were measured,

| Tensile, | Elong., | Modulus, | psi | Tear, Die C | Hardness |
|---|---|---|---|---|---|
| psi | % | 100% | 300% | pli | Shore A |
| 6830 | 410 | 785 | 2270 | 376 | 78 |

EXAMPLE 7

This Example illustrates the proposition that a variety of isocyanates can be used to prepare the isocyanate-terminated polyurethane prepolymer and that such prepolymer is readily cured by the triazine curing agents described herein.

A. A prepolymer having 4.3% NCO was prepared from 83.9 parts of a polyethylene-propylene adipate having 1404 equiv. wt., 9.7 parts Hylene TM, and 6.4 parts of a polymeric [4-isocyanato phenyl] methane (MDI) having a functionality of about 2.7 and an equivalent weight of 135, sold by Upjohn and Company under the name PAPI 135. To 100 grams of this molten prepolymer was added 10.3 grams of n-hexylmelamine at 212° F. The formulation was poured into a 6″ × 6″ pre-heated mold and compression-molded at 240° F. for 1 hour, following a gel time of 12 minutes. A transparent amber sheet having good hot dimensional stability was obtained. The sheet was subsequently post-cured for 16 hrs. at 212° F., and the following physical properties were measured,

| Tensile, | Elong., | Modulus, | | | Tear, | Hardness |
|---|---|---|---|---|---|---|
| psi | % | 100% | 300% | 500% | pli | Shore A |
| 7035 | 595 | 690 | 1535 | 4615 | 461 | 79 |

B. A prepolymer having 5.2% NCO was prepared from 77.6 parts of a polyethylene adipate having 805 equiv. wt., 13.7 parts of Hylene TM, 2.8 parts of MDI and 5.9 parts PAPI 135 (polymeric MDI, f=2.7). To 100 grams of this molten prepolymer was added 12.3 grams of molten n-hexylmelamine at 212° F. The formulation was poured into a 6″ × 6″ pre-heated mold and compression-molded at 240° F. for 1 hour, following a gel time of 9 minutes. A transparent amber sheet with good hot dimensional stability was obtained. It was subsequently post-cured for 16 hrs/212° F. and the following physical properties were measured,

| Tensile | Elong., | Modulus, | | | Tear, | Hardness |
|---|---|---|---|---|---|---|
| psi | % | 100% | 300% | 500% | pli | Shore A |
| 7200 | 520 | 955 | 2160 | 6455 | 545 | 85 |

EXAMPLE 8

This Example illustrates the capacity of the substituted di- and triamino-s-triazines described herein to cure resin mixtures and blends. Also illustrated in the proposition that resin blends can be adjusted to moderate and control the curing time.

Varying amounts of the indicated isocyanate-terminated polyurethane prepolymers were combined in the molten state with n-hexylmelamine to provide a ratio NCO/NH$_2$ of 0.96 for all runs. The mixture was poured into a pre-heated 6″ × 6″ mold, and cured and postcured as indicated.

| Resin Composition* | | | | | | |
|---|---|---|---|---|---|---|
| A (4.34% NCO) | 100 | 75 | 75 | 60 | 60 | 55 |
| B (5.53% NCO) | — | — | 25 | 25 | 20 | 15 |
| C (30.66% NCO) | — | 25 | — | 15 | 20 | 30 |
| NCO/NH$_2$ | 0.96 | 0.96 | 0.96 | 0.96 | 0.96 | 0.96 |
| Cure Conditions | | | | | | |
| Cure Time at 212° F | 16hrs. | 2hr. 6min. | 2hr. 12min. | 55min. | 47min. | 34min. |
| Post Cure at 212° F | None | 16hrs. | 16hrs. | 16hrs. | 16hrs. | 16hrs. |
| Physical Properties (After 2 weeks at R.T.) | | | | | | |
| Tensile, psi | 5465 | 5300 | 4735 | 5050 | 5115 | 5120 |
| Elongation, % | 595 | 570 | 615 | 565 | 545 | 485 |
| Hardness, Shore A | 87 | 90 | 83 | 91 | 91 | 95 |
| Modulus, psi | | | | | | |
| 100% | 1045 | 1130 | 855 | 1085 | 1115 | 1380 |
| 200% | 1455 | 1525 | 1155 | 1450 | 1500 | 1805 |
| 300% | 1965 | 2050 | 1555 | 2005 | 2125 | 2595 |
| 400% | 2775 | 2990 | 2320 | 3005 | 3230 | 3740 |
| 500% | 4075 | 4350 | 3485 | 4255 | 4465 | — |
| Tear, Die C, pli | 675 | 646 | 546 | 596 | 598 | 642 |

*A is the TDI-terminated polyester prepolymer of Example 2
B is the MDI-terminated polyester prepolymer of Example 5
C is the Polyphenylene isocyanate described in Example

EXAMPLE 9 curing agents of this invention provide a product having a significantly better Bashore Rebound.

| Formulation | 4,4'-methylene bis(2-chloroaniline) | | | n-hexylmelamine | | |
|---|---|---|---|---|---|---|
| Adiprene L-100, 4.17% NCO | 100 | 100 | 100 | 100 | 100 | 100 |
| 4,4'-methylenebis (2-chloroaniline) | 11.3 | 12.6 | 14.0 | — | — | — |
| n-hexylmelamine | — | — | — | 8.9 | 9.9 | 10.9 |
| % Stoichiometry* | 85 | 95 | 105 | 85 | 95 | 105 |
| Cure Conditions | | | | | | |
| Pot life at 212° F, min. | 9–10 | 9–10 | 7–8 | 7–8 | 7–8 | 6–7 |
| Mold Closing Time, min. | 16 | 16 | 15 | 130 | 130 | 125 |
| Cured (Mold) 212° F | hr. | hr. | hr. | 16 hrs. | 16 hrs. | 16 hrs. |
| Cured (Post) 212° F | 16 hrs. | 16 hrs. | 16 hrs. | No | No | No |
| Aged at Room Temp. | No | No | No | 2 wks. | 2 wks. | 2 wks. |
| Physical Properties | | | | | | |
| % Modulus, 100 psi | 1120 | 1000 | 1200 | 1200 | 1130 | 1110 |
| % Modulus, 200 psi | 1590 | 1400 | 1490 | 1780 | 1690 | 1550 |
| % Modulus, 300 psi | 2325 | 2000 | 1795 | 2490 | 2300 | 1900 |
| % Modulus, 400 psi | — | — | 2285 | — | 3350 | 2500 |
| % Modulus, 500 psi | — | — | 3210 | — | — | — |
| Tensile, psi | 2980 | 3200 | 4025 | 3550 | 4400 | 3380 |
| Elongation, % | 340 | 390 | 570 | 360 | 450 | 480 |
| Tear, Die C, pli | 475 | 490 | 595 | 475 | 505 | 560 |
| Hardness, Shore "A" | 90 | 89 | 90 | 85 | 85 | 85 |
| Compression Set % | 23 | 27 | 37 | 21 | 30 | 35 |
| (Method B 22 hrs/158° F) | | | | | | |
| Bashore Rebound, % (80° F) | 43 | 40 | 42 | 58 | 55 | 56 |
| Compression/Deflection, psi at 5% Deflection | 290 | 280 | 280 | 130 | 120 | 140 |
| at 10% Deflection | 530 | 500 | 510 | 275 | 245 | 280 |
| at 15% Deflection | 680 | 640 | 660 | 430 | 390 | 430 |
| 20% Deflection | 820 | 770 | 780 | 605 | 550 | 600 |
| at 25% Deflection | 980 | 920 | 920 | 800 | 730 | 790 |

* $\frac{\text{Equiv. NH}_2}{\text{Equiv. NCO}} \times 100$. Functionality of n-hexylmelamine considered to be 2.0

This Example illustrates the use of the substituted di- and triamino-s-triazines to cure polyether based polymer.

A. To 100 parts by weight of the pre-heated (212° F.) polyether polyol prepolymer based on 1,4-butane diol ether (polytetrahydrofuran), sold by E. I. DuPont de Nemours & Co., Wilmington, Delaware as Adiprene L-100, containing 4.17% NCO were added the indicated amount of curing agent. The mixture was poured into a preheated 6" × 6" mold and compression molded under the indicated conditions; the indicated physical properties were obtained. It is seen that most of the properties of the elastomer cured with the curing agent of this invention are comparable to those obtained with 4,4'-methylene bis(2-chloroaniline) except that the B. 100 grams of the polyether-based prepolymer Adiprene L-167 having a structure comparable to Adiprene L-100 above but having 6.4% NCO was blended with 17.1 grams of N$^2$, N$^2$-di-n-butylmelamine at 212° F. The formulation was poured into a 6" × 6" mold, and gelled at 212° F. over a 2½ hr. period. Following compression-molding 16 hrs/212° F. a transparent colorless sheet was obtained which was then aged at room temperature for two weeks. The following properties were measured on the sheet,

| Tensile, psi | Elong., % | Modulus, psi 100% | 200% | 300% | Tear, Die C pli | Hardness Shore A |
|---|---|---|---|---|---|---|

-continued

| Tensile, | Elong., | Modulus, psi | | Tear, Die C | Hardness |
|---|---|---|---|---|---|
| 4600 | 380 | 440 | 800 1880 | 236 | 70 |

EXAMPLE 10

This Example illustrates the use of the triazine curing agents to cure a mixture of polyester and polyether-based prepolymers.

To 100 grams of a TDI-terminated prepolymer of polyethylene-propylene adipate and poly(propylene glycol) blended in equal parts, having 7.50% NCO, was added 25.5 grams of molten n-hexylmelamine at 212° F. The formulation was poured into a 6" × 6" sheet mold and compression-molded at 212° F. for 1 hour following a gel time of seven minutes at 212° F. The clear, colorless sheet was post-cured 16 hrs. at 212° F. and aged two weeks at room temperature. The following physical properties were measured.

| Tensile, psi | Elong., % | Modulus, psi 100% | 300% | Tear, Die C pli | Hardness Shore A/D |
|---|---|---|---|---|---|
| 5700 | 480 | 2300 | 4120 | 868 | 97/56 |

EXAMPLE 11

This Example illustrates the use of the reaction product of 2 moles of n-hexylmelamine with 1 mole of toluene diisocyanate to cure polyurethane prepolymers.

12.3 grams of the product isolated from the addition, at high dilution, of 1 mole of TDI to 2 moles n-hexylmelamine, 6.81 grams of n-hexylmelamine, and 100 grams of a TDI-capped prepolymer of polyethyleneadipate having 4.29% NCO, were melted and combined at 285° F. The formulation was poured into a preheated mold, with rapid gelling, and compression-molded 16 hrs. at 265° F. A clear amber-colored sheet was obtained having the following properties,

| Tensile, psi | Elong., % | Modulus, psi 100% | 300% | Tear, Die C pli | Hardness Shore A |
|---|---|---|---|---|---|
| 2500 | 440 | 1015 | 1840 | 589 | 85 |

EXAMPLE 12

The urethane elastomers cured with the curing agents of this invention have been found to exhibit substantially improved lightfastness compared to products cured with 4,4'-methylenebis (2-chloroaniline).

Urethane sheets were molded at 212° F. from the toluene diisocyanate terminated polyester polyol of Example 3 and cured with 4,4'-methylenebis (2-chloroaniline) and n-hexylmelamine, separately, at a stoichiometry of 1.05 NCO equivalents per NH$_2$ equivalent. From each sheet a strip was cut, approximately 1" × 6" and mounted so that half of each strip was masked. These were exposed to a sunlamp for 16 hours. At the end of that period it was observed that the exposed portion of the urethane cured with 4,4'-methylenebis (2-chloroaniline) had discolored to a deep yellow-amber while the urethane cured with n-hexylmelamine remained transparent and virtually unaffected by the exposure.

EXAMPLE 13

This Example illustrates a "one-shot" urethane cured with the curing agents of this invention.

A. To 87.0 grams of a poly(ethylene adipate) diol having a molecular weight of 1227 and 2.7 grams trimethylolpropane that had been conditioned at 100° C., were added 32.0 grams of Hylene TM, and a molten blend of 11.6 grams of n-hexylmelamine, 5.3 grams of the bismelamine of Example 1F and 0.6 grams of triethylene diamine. These ingredients were mixed together and poured into a preheated 6" × 6" mold. The mold was closed immediately and the formulation was pressed out for one hour at 240° F. A clear, colorless sheet having excellent hot dimensional stability and Shore A hardness of 93 was obtained. Following 16 hrs. post-cure at 212° F., the following physical properties were measured.

| Tensile, psi | Elong., % | Modulus, psi 100% | 200% | Tear pli | Duro Shore A/D |
|---|---|---|---|---|---|
| 5125 | 245 | 1975 | 3215 | 495 | 95/46 |

B. To 73.4 grams of a poly(tetramethylene ether) diol having a molecular weight of 2070 and 1.34 grams of trimethylolpropane that had been conditioned at 100° C., were added 16.0 grams of Hylene TM, and a molten blend of 5.8 grams of n-hexylmelamine and 2.6 grams of the bismelamine of Example 1F. These ingredients were mixed together and poured into a heated 6" × 6" mold. The mold was closed immediately and the formulation was pressed out for one hour at 240° F. An opaque white sheet having excellent hot dimensional stability and Shore A hardness of 85 was obtained. Following 16 hrs. post-cure at 212° F., the following physical properties were measured.

| Tensile, psi | Elong. % | Tear, Die C pli | Hardness Shore A/D |
|---|---|---|---|
| 1100 | 50 | 244 | 90/37 |

EXAMPLE 14

A. 100 grams of a molten prepolymer prepared from poly(ethylene adipate) diol and tolylene diisocyanate and having 4.4% NCO was combined with 9.0 grams of molten n-butylmelamine at 212° F. The formulation was poured into a 6" × 6" preheated mold and compression-molded for 16 hrs./212° F. following a gel time of 33 minutes at 212° F. A clear, colorless sheet was obtained. The following properties were measured after the sheet was aged at room temperature for two weeks.

| Tensile, | Elong., | Modulus, psi | | Tear, Die C | Hardness |
|---|---|---|---|---|---|
| 7660 | 585 | 1245 | 2470 5260 | 676 | 86/35 |

B. 25 grams of a molten prepolymer prepared from poly(ethylene adipate) diol and tolylene diisocyanate and having 4.4% NCO was combined with 2.5 grams of molten (3-methoxypropyl) melamine at 212° F. The formulation was poured into a preheated mold having two 2″ × 2″ cavities and compression-molded for 16 hrs. at 212° F. following a gel time of 45 minutes at 212° F. Clear, colorless strong cures were obtained having 77 Shore A hardness.

EXAMPLE 15

Cure of a prepolymer with a curvative blend of n-hexylmelamine and methylenebis [oxyethyl melamine]

100 grams of a molten prepolymer prepared from poly(ethylene adipate) diol and tolylene diisocyanate and having 4.4% NCO was combined at 212° F. with a molten blend of 8.5 grams n-hexylmelamine and 1.8 grams of the bismelamine obtained from the reaction of 2,4-diamino-6-chlorotriazine with bis [2-aminoethyl] formal. The formulation was poured into a preheated 6″ × 6″ mold and compression-molded for 1 hour at 240° F. following a gel time of 20 minutes at 240° F. The clear, colorless sheet was post-cured for 16 hrs./212° F., and the following properties were measured.

| Tensile, psi | Elong. % | Modulus, psi 100% | 300% | 500% | Tear, Die C pli | Hardness Shore A/D |
|---|---|---|---|---|---|---|
| 7170 | 510 | 920 | 2085 | 6275 | 503 | 80/30 |

EXAMPLE 16

$N^2, N^4$-Dihexylmelamine

Cyanuric chloride is treated with ammonia to prepare monoamino-di-chloro-s-triazine, which is then treated with n-hexylamine to give the title product as a viscous liquid.

Analysis for: $C_{15}H_{30}N_6$: Calculated: C, 61.19; H, 10.27; N, 28.54: Found: C, 59.56, 59.35; H, 10.98, 10.76; N, 27.79, 27.99.

EXAMPLE 17

The following Example illustrates the use of the product of Example 16 as a curing agent.

$N^2, N^4$-dihexylmelamine (15.0 gm) and a polyester TDI prepolymer (100 g) were pressed out at 212° F. for 23 hours. A thermoplastic cured product was obtained.

EXAMPLE 18

The following Example illustrates the use of a bismelamine as sole curative, and a rapid cure using a mono substituted melamine.

A polyester TDI prepolymer having 5.7% NCO was cured with the curatives shown in the absence of a cure catalyst. The cure conditions andd the properties obtained are also tabulated.

| Curing Agent | n-hexylmelamine | bis-melamine from Ex. 1 (F) |
|---|---|---|
| Amount of curing agent per 100 grams prepolymer | 13.6 | 17.7 |
| Temperature of cure | 300° F. | 260° F. |
| Gel time | 8 min. | 1 min. |
| Cure cycle | ½ hr./300° F | ½ hr./260° F |
| Post-cure | 16 hrs/212° F | 16 hrs/212° F |
| Physical Properties | | |
| Tensile | 8175 psi | 4220 psi |
| Elongation | 560% | 185% |
| Hardness Shore A/D | 90/36 | 95/40 |
| 100% Modulus | 1230 psi | 1950 psi |
| 300% Modulus | 2925 psi | — |

-continued

| Curing Agent | n-hexylmelamine | bis-melamine from Ex. 1 (F) |
|---|---|---|
| Tear, Die C | 705 pli | 430 pli |

EXAMPLE 19

The following Example illustrates the use of conventional urethane metering equipment to process urethane resins based on the curatives of this invention.

A polyester TDI prepolymer having 7.0% NCO and a blend of substituted melamine and bismelamine curatives were processed through conventional commercial urethane metering machinery, and the metered mix used to cast solid parts and test sheets. The reactants were n-hexylmelamine (8.4 parts), the bismelamine of Example 1 (F) (3.6 parts), and resin (100 parts).

The following properties were found on a test sheet cured 1 hour at 212° F. and post-cured 16 hours at 212° F.

| Tensile | 7200 psi |
|---|---|
| Elongation | 310% |
| Hardness A/D | 95/52 |
| 100% Modulus | 2400 psi |
| 200% Modulus | 3780 psi |
| 300% Modulus | 6420 psi |
| Tear | 840 pli |
| Compression Set, ASTM Method B | 24% |
| Compression Deflection, 25% Compression | 1725 psi |

A solid wheel demolded after curing 22 minutes/240° F., and then post-cured 16 hrs/212° F. was clear, colorless, void-free, and had a Shore Hardness of 62 D.

EXAMPLE 20

The following Example illustrates the use of a conventional polyol as a co-curative.

To a polyester TDI prepolymer (100 grams) having 7.5% NCO was added a blend of n-hexylmelamine (3.4g), the bismelamine of Example 1 (F) (3.7 g), and trimethylolpropane (5.1 g). Cure conditions and physical properties are tabulated. No cure catalyst was used.

| Temperature of Cure | 212° F |
|---|---|
| Gel Time | 8 min. |
| Cure cycle | 30 min./212° |
| Post-cure cycle | 16 hrs./212° |
| Physical properties | |
| Tensile | 5250 psi |
| Elongation | 230% |
| Hardness Shore A/D | 95/53 |
| 100% Modulus | 2100 psi |
| 200% Modulus | 3890 psi |
| Tear, Die C | 450 pli |
| Compression set, ASTM Method B | 19% |
| Appearance | Clear, Colorless |

EXAMPLE 21

A. Bisphenyl A diglycidyl ether (1 mole) is treated with n-hexylmelamine (2.5 moles) to give a curative having the composition:

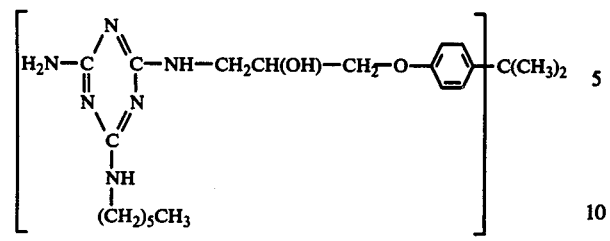

(1 moles) and

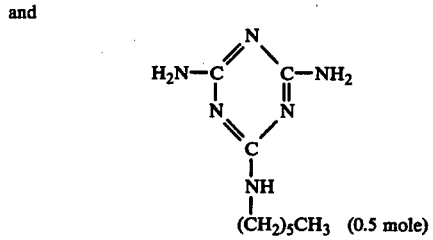

B. A polyester TDI prepolymer having 4.4% NCO (100 g), curative from part A (28.5 g) and dipropylene glycol dibenzoate (25 g) were combined at 212° F. Immediate homogeneous gellation occurred. No cure catalyst was used.

EXAMPLE 22

Following a procedure analogous to that of Ames et al., in Proc. Nat. Acad. Sci., 70, 2281 (1971) and Ames in *Chemical Mutagens:Principles and Methods for Their Detection* A. Hollaender (Ed) Plenum Press, New York and London (1971) as reported in Chemical and Engineering News, Pg. 19, Dec. 22, 1975, n-hexylmelamine, the bismelamine of Example 1F and 4,4'-methylenebis-(2-chloroaniline) were tested against selected strains of Saccharomyces cerevisiae and samonella typhimurium either with the aid of activation by rat liver enzymes or unactivated. n-Hexylmelamine and the bismelamine of Example 1F were not mutagenic to any of the strains tested at concentrations where the compounds showed moderate toxicity to the organism nor at any dose level tested. The exhibition of toxicity indicates that physiologically active dose levels were employed. 4,4'-methylenebis-(2-chloroaniline) showed mutagenicity against salmonella typhimurium TA 100 when activated by rat liver microsomal enzyme preparations. The activity was moderately strong and dose related.

What is claimed is:

1. A curable composition comprising:
   (a) an isocyanate-terminated polyurethane prepolymer and
   (b) a compound of formula

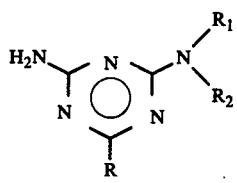

where R is

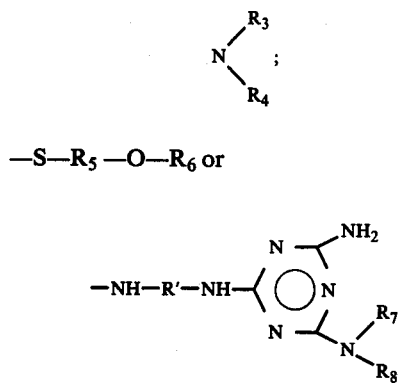

—S—$R_5$—O—$R_6$ or

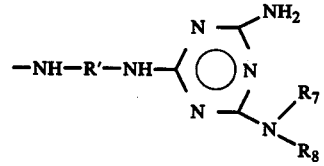

where at least one of $R_1$, $R_2$, $R_3$, and $R_4$ is hydrogen, $R_1$, $R_2$, $R_3$, $R_4$, $R_5$, $R_6$, $R_7$ and $R_8$ each independently is hydrogen or an optionally substituted aliphatic or aromatic group, provided however that said aliphatic or aromatic group may not be substituted with hydroxy and that $R_1$, $R_2$, $R_3$, $R_4$, $R_5$, and $R_6$ may not have ethylenic $>C=C<$ bonds;

R' is the divalent residue of an organic diamine, the residue of an organic diisocyanate, or the residue of an organic diepoxide, and where all $R_1$, $R_2$, $R_3$, $R_4$, $R_5$ and $R_6$ are not all simultaneously hydrogen provided however when R is

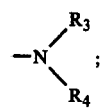

that $R_1$, $R_2$, $R_7$ and $R_8$ can all be hydrogen, that $R_1$ and $R_2$ may contain ethylenic $>C=C<$ bonds; and that if either member of the pairs $R_1$, $R_2$ or $R_7$, $R_8$ contains ethylenic $>C=C<$ bonds, the other member of the same pair must be hydrogen.

2. A curable composition according to claim 1 wherein when R is $$-N\begin{matrix}R_3\\R_4\end{matrix};$$

—S—$R_5$; or —O—$R_6$ at least one of $R_1$, $R_2$, $R_3$, $R_4$, is hydrogen and $R_1$, $R_2$, $R_3$, $R_4$, $R_5$ and $R_6$ each independently is:

(A) hydrogen;
(B) alkyl of 1 to 24 carbon atom;s
(C) alkynyl of 3 to 24 carbon atoms; or
(D) cycloalkyl of 3 to 10 carbon atoms; or when R is

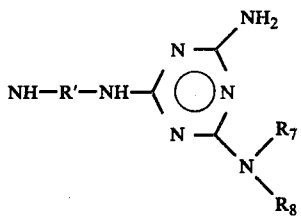

at least one of $R_1$, $R_2$ is hydrogen and $R_1$, $R_2$, $R_7$ and $R_8$ each independently is:
(A) hydrogen;
(B) alkyl of 1 to 24 carbon atoms;
(C) alkynyl of 3 to 24 carbon atoms;
(D) cycloalkyl of 3 to 10 carbon atoms; or
(E) alkenyl of 3 to 24 carbon atoms; said (B) alkyl; (C) alkenyl; (D) cycloalkyl; or (E) alkenyl being unsubstituted or substituted by:
 (a) alkoxy of 1 to 18 carbon atoms,
 (b) the acyl residue of an aliphatic carboxylic acid of 2 to 18 carbon atoms or of an aromatic carboxylic acid containing 6 or 10 carbon atoms in the aromatic nucleus,
 (c) acyloxy, where the acyl moiety is as previously defined,
 (d) carbalkoxy of 3 to 20 carbon atoms,
 (e) carboaryloxy where the aryl moiety contains 6 or 10 carbon atoms in the aromatic nucleus,
 (f) alkylcarbonyldioxy containing 1 to 18 carbon atoms in the alkyl moiety.
 (g) arylcarbonyldioxy where the aryl moiety contains 6 or 10 carbon atoms in the aromatic nucleus,
 (h) amino, carbamoyl, sulfamoyl that are unsubstituted or substituted on the nitrogen atoms by:
  1 or 2 radicals independently selected from (i) alkyl of 1 to 18 carbon atoms, (ii) cycloalkyl of 3 to 8 carbon atoms, (iii) aryl of 6 or 10 carbon atoms in the aryl nucleus and (iv) acyl as previously defined and where said radicals (i, ii, iii, and iv) are further unsubstituted or substituted by chloro, fluoro, iodo, bromo, amino, lower alkoxy, carbamoyl, sulfamoyl, lower alkylthio, perfluoroalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano,
 (i) chloro, fluoro, bromo, iodo, perhaloalkyl of 1 to 12 carbon atoms, oxo, nitro, cyano, thiocyano,
 (j) alkylthio of 1 to 18 carbon atoms,
 (k) arylthio of 6 or 10 carbon atoms in the aryl nucleus,
 (l) alkylsulfinyl of 1 to 18 carbon atoms,
 (m) arylsulfinyl of 6 to 10 carbon atoms in the aryl nucleus,
 (n) alkylsulphonyl of 1 to 18 carbon atoms,
 (o) arylsulphonyl of 6 or 10 carbon atoms in the aryl nucleus,
 (p) alkylphosphoryl of 1 to 18 carbon atoms,
 (q) arylphosphoryl of 6 or 10 carbon atoms in the aryl nucleus,
 (r) alkylthiophosphoryl of 1 to 18 carbon atoms,
 (s) arylthiophosphoryl of 6 or 10 carbon atoms in the aryl nucleus,
 (t) cycloalkyl of 3 to 10 carbon atoms,
 (u) cycloalkyloxy of 3 to 10 carbon atoms,
 (v) phenyl or naphthyl,
 (w) acylamino where the acyl moiety is as previously defined,
 (x) alkylureido of 1 to 18 carbon atoms,
 (y) arylureido of 6 or 10 carbon atoms in the aryl nucleus,
 (z) silyl of formula

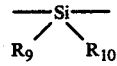

where $R_9$, $R_{10}$ and $R_{11}$ each independently is branched or unbranched alkyl of 1 to 6 carbon atoms, cycloalkyl of 3 to 7 carbon atoms, phenylalkylene of 1 to 6 carbon atoms in the alkyl group, phenyl or alkyl phenylene of 1 to 6 carbon atoms in the alkyl group, or where $R_1$, $R_2$, $R_3$, $R_4$, $R_5$, $R_6$, $R_7$ and $R_8$ each independently is
(F) aryl of 6 or 10 carbon atoms that is unsubstituted or substituted by one to three of:
 (a) alkyl of 1 to 18 carbon atoms,
 (b) cycloalkyl of 3 to 8 carbon atoms,
 (c) alkoxy of 1 to 18 carbon atoms,
 (d) chloro, bromo, iodo, fluoro, perhaloalkyl of 1 to 12 carbon atoms nitro, cyano, thiocyano, alkylthio of 1 to 18 carbon atoms,
 (e) arylthio of 6 or 10 carbon atoms in the aryl nucleus,
 (f) amino, sulfamoyl, carbamoyl or said amino, sulfamoyl or carbamoyl containing
  one or two substituents on the nitrogen atom selected from (i) alkyl of 1 to 18 carbon atoms, (ii) cycloalkyl of 3 to 8 carbon atoms, (iii) aryl of 6 or 10 carbon atoms in the aryl nucleus or (iv) acyl as previously defined, and where said nitrogen substituents (i, ii, iii, and iv) are further unsubstituted or substituted by chloro, fluoro, iodo, bromo, amino, lower alkoxy, carbamoyl, sulfamoyl, lower alkylthio, perfluoroalkyl of 1 to 12 carbon atoms, acyl of 2 to 5 carbon atoms, acylamino of 2 to 5 carbon atoms, nitrile, nitro, and thiocyano.
 (g) the acyl residue of an aliphatic carboxylic acid of 2 to 18 carbon atoms or of an aromatic carboxylic acid containing 6 or 10 carbon atoms in the aryl nucleus,
 (h) carbalkoxy of 2 to 18 carbon atoms,
 (i) carboaryloxy containing 6 or 10 carbon atoms in the aryl nucleus,
 (j) acylamino where acyl is as previously defined,
 (k) phenyl, naphthyl, phenoxy, naphthoxy,
 (l) phenylthio, phenylimino, phenylmethylene,
 (m) phenylsulfonyl, and where said hydrocarbyl substituents on the alkyl, alkenyl, alkynyl, cycloalkyl and aryl groups can be further substituted by chloro, fluoro, iodo, bromo, amino, lower alkoxy, carbamoyl, sulfamoyl, lower alkylthio, perfluoroalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano, or where one of the pairs of $R_1$, $R_2$ or $R_3$, $R_4$ or one or both of $R_1$, $R_2$ and $R_7$, $R_8$ can together with their associated nitrogen atom form morpholinyl, piperidyl, piperazyl, or pyrrolidinyl; and where R' is alkylene of
(A) 2 to 24 carbon atoms,
(B) alkenylene of 4 to 24 carbon atoms, (C) alkynylene of 4 to 24 carbon atoms,
(D) cycloalkylene of 4 to 10 carbon atoms, or said radical A, B, C or D substituted by lower alkyl, lower alkoxy, chloro, fluoro, iodo, bromo, amino, lower alkoxy, carbamoyl, sulfamoyl, lower alkythio, perhaloalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano, or where R' is poly(alkylene oxide) of 5 to 20 carbon atoms and where said alkylene contains 2 to 5 carbon atoms, or where R' is
(A) phenylene,
(B) diphenylene ether,
(C) diphenylene thioether,
(D) diphenyleneimino,
(E) diphenylene (lower) alkylene, or
(F) diphenylene sulfone that is unsubstituted or substituted on the aryl moiety (of A, B, C, D, E or F) by 1 to 3 of lower alkyl, cycloalkyl of 3 to 8 carbon atoms, lower alkoxy, chloro, bromo, fluoro, perhaloalkyl of 1 to 12 carbon atoms, nitro, cyano, thiocyano, alkylthio of 1 to 18 carbon atoms, amino, sulfamoyl, carbamoyl or said amino, sulfamoyl or carbamoyl containing one or two substituents on the nitrogen atom selected from
(a) alkyl of 1 to 18 carbon atoms,
(b) cycloalkyl of 3 to 8 carbon atoms,
(c) aryl of 6 or 10 carbon atoms in the aryl nucleus or
(d) acyl as previously defined, and where said nitrogen substituents (a, b, c or d) are further unsubstituted or substituted by chloro, fluoro, iodo, bromo, amino, lower alkoxy, carbamoyl, sulfamoyl, lower alkylthio, perfluoroalkyl of 1 to 12 carbon atoms, acyl of 2 to 5 carbon atoms, carbalkoxy of 2 to 5 carbon atoms, acylamino of 2 to 5 carbon atoms, nitrile, nitro and thiocyano,
or where R' is alkylene interrupted by methylenedioxy or where R' is the residue of an organic diisocyanate of formula

OCN—B—NCO where B is aliphatic, aromatic or aliphatic-aromatic, or a polyurethane prepolymer
or where R' is the residue of an organic diepoxide of the formula:

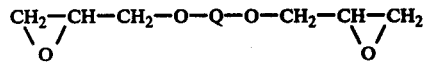

wherein Q is
(A) phenylene,
(B) diphenylene ether,
(C) diphenylene thioether,
(D) diphenyleneimino,
(E) diphenylene (lower) alkylene or
(F) diphenylene sulfone that is unsubstituted or substituted on the aryl moiety (of A, B, C, D, E or F) by 1 to 3 of lower alkyl, cycloalkyl of 3 to 8 carbon atoms, lower alkoxy, chloro, bromo, fluoro, perhaloalkyl of 1 to 12 carbon atoms, nitro, cyano, thiocyano, alkylthio of 1 to 18 carbon atoms, amino, sulfamoyl, carbamoyl, or said amino, sulfamoyl, or carbamoyl containing one or two substituents on the nitrogen atom selected from (a) alkyl of 1 to 18 carbon atoms,
(b) cycloalkyl of 3 to 8 carbon atoms,
(c) aryl of 6 or 10 carbon atoms in the aryl nucleus, or
(d) acyl as previously defined, and where said nitrogen substituents (a, b, c or d) are further unsubstituted or substituted by chloro, fluoro, iodo, bromo, amino, lower alkoxy, carbamoyl, sulfamoyl, lower alkyl thio, perfluoroalkyl of 1 to 12 carbon atoms, acyl of 2 to 5 carbon atoms, carbalkoxy of 2 to 5 carbon atoms, acyl amino of 2 to 5 carbon atoms, nitrile, nitro and thiocyano, or where Q is
(A) alkylene of 2 to 24 carbon atoms,
(B) alkenylene of 4 to 24 carbon atoms,
(C) alkynylene of 4 to 24 carbon atoms,
(D) cycloalkylene of 4 to 10 carbon atoms, or said radical (A, B, C or D) substituted by lower alkyl, lower alkoxy, chloro, fluoro, iodo, bromo, amino, lower alkoxy, carbamoyl, sulfamoyl, lower alkyl thio, perhaloalkyl of 1 to 12 carbon atoms, acyl of 2 to 5 carbon atoms, carbalkoxy of 2 to 5 carbon atoms, acylamino of 2 to 5 carbon atoms, nitrile, nitro or thiocyano, and where all of $R_1$, $R_2$, $R_3$, $R_4$, $R_5$ and $R_6$ are not simultaneously hydrogen provided however that when

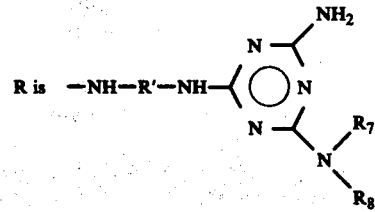

$R_1$, $R_2$, $R_7$ and $R_8$ can all be hydrogen.

3. A curable composition according to claim 2 in which

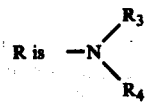

or 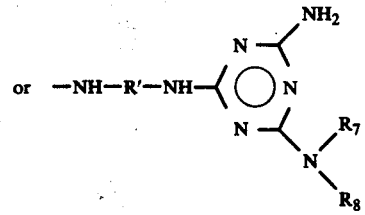

4. A curable composition according to claim 3 in which when R is

$R_1$, $R_2$, $R_3$ and $R_4$ each independently is hydrogen, or alkyl of 1 to 24 carbon atoms; or when R is 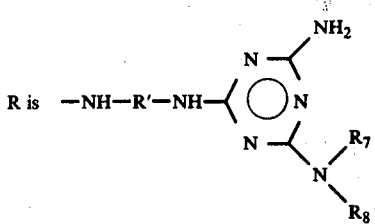

R$_1$, R$_2$, R$_7$ and R$_8$ each independently is hydrogen, alkyl of 1 to 24 carbon atoms or alkenyl of 3 to 24 carbon atoms;

said alkyl or alkenyl being unsubstituted or substituted by chloro, bromo, carboloweralkoxy, lower alkoxy, acyl or acyloxy of 2 to 5 carbon atoms, amino, carbamoyl or sulfamoyl that are unsubstituted or substituted on the nitrogen atom by one or two radicals independently selected from lower alkyl, cycloalkyl of 4 to 7 carbon atoms, phenyl, acyl of 2 to 5 carbon atoms or where said nitrogen substituents together with the associated nitrogen atom form morpholinyl, piperidyl and where said nitrogen substituents are further unsubstituted or substituted by chloro, amino, lower alkoxy, carbamoyl, sulfamoyl, acyl, acylamino or carbalkoxy of 2 to 5 carbon atoms, nitro or nitrile cyano, phenyl or acylamino of 2 to 5 carbon atoms or where R$_1$, R$_2$, R$_3$, R$_4$, R$_7$ and R$_8$ each independently is phenyl or naphthyl that is unsubstituted or substituted by one to three of lower alkyl, lower alkoxy, chloro, bromo, nitro, cyano, amino, sulfamoyl or carbamoyl that is unsubstituted or substituted on the nitrogen atom by one or two radicals selected from lower alkyl, phenyl and acyl of 2 to 5 carbon atoms, said substituents being further unsubstituted or substituted by chloro, lower alkyl, lower alkoxy, amino, carbamoyl, sulfamoyl, acyl, acylamino or carbalkoxy of 2 to 5 carbon atoms, or cyano, acyl or acylamino of 2 to 5 carbon atoms, carboloweralkoxy, or where one of the pairs R$_1$-R$_2$ or R$_3$-R$_4$, or one or both of R$_1$-R$_2$ and R$_7$-R$_8$ together with the associated nitrogen atom forms morpholinyl, piperidyl, or piperazyl.

5. A curable composition according to claim 4 in which R is

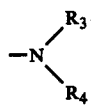

and

R$_1$, R$_2$, R$_3$ and R$_4$ each independently is hydrogen, alkyl of 1 to 24 carbon atoms that is unsubstituted or substituted by lower alkoxy chloro, lower alkoxycarbonyl, cyano, amino, N-lower alkylamino, N,N-diloweralkylamino, piperidyl, morpholinyl and phenyl, or where one of the pairs of R$_1$-R$_2$ and R$_3$-R$_4$ together with the associated nitrogen atom form morpholinyl, or piperidyl and where all of R$_1$, R$_2$, R$_3$ and R$_4$ are not simultaneously hydrogen.

6. A curable composition according to claim 5 in which R$_1$, R$_2$, R$_3$ and R$_4$ each independently is hydrogen or alkyl of 4 to 24 carbon atoms that is unsubstituted or substituted by lower alkoxy.

7. A curable composition according to claim 3 in which R is

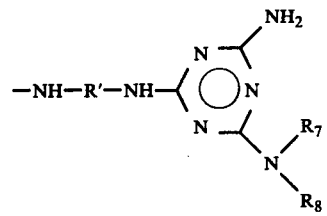

8. A curable composition according to claim 7 in which R$_1$, R$_2$, R$_7$ and R$_8$ each independently is hydrogen, alkyl of 1 to 24 carbon atoms, alkenyl of 3 to 24 carbon atoms, said alkyl or alkenyl being unsubstituted or substituted by chloro, bromo, carboloweralkoxy, lower alkoxy, acyl or acyloxy of 2 to 5 carbon atoms, amino, carbamoyl or sulfamoyl that are unsubstituted or substituted on the nitrogen atom by one or two radicals independently selected from lower alkyl, cycloalkyl of 4 to 7 carbon atoms, phenyl, acyl of 2 to 5 carbon atoms or where said nitrogen substituents together with the associated nitrogen and form morpholinyl, piperidyl or piperazyl and where said nitrogen substituents are further unsubstituted or substituted by chloro, amino, lower alkoxy, carbamoyl, sulfamoyl, acyl, acylamino or carbalkoxy of 2 to 5 carbon atoms, nitro or nitrile, cyano, phenyl or acylamino of 2 to 5 carbon atoms or where R$_1$, R$_2$, R$_7$ and R$_8$ each independently is phenyl or naphthyl that is unsubstituted or substituted by one to three of lower alkyl, lower alkoxy, chloro, bromo, nitro, cyano, amino, sulfamoyl or carbamoyl that is unsubstituted or substituted on the nitrogen atom by one or two radicals selected from lower alkyl, phenyl and acyl of 2 to 5 carbon atoms, said chloro, lower alkyl, lower alkoxy, amino, carbamoyl, sulfamoyl, acyl, acylamino or carbalkoxy of 2 to 5 carbon atoms, or cyano, acyl or acylamino of 2 to 5 carbon atoms, carboloweralkoxy, or where one of the pairs R$_1$-R$_2$ or R$_7$-R$_8$, together with the associated nitrogen atom forms mopholyl, piperidyl, or piperazyl, R' is alkylene of 2 to 18 carbon atoms, poly(alkylene oxide), alkylene of 2 to 18 carbon atoms interrupted by methylene dioxy, or R' is diphenylene methane or the residue of an organic diisocyanate.

9. A curable composition according to claim 8 in which R$_1$, R$_2$, R$_7$ and R$_8$ are hydrogen and R' is alkylene of 2 to 18 carbon atoms, poly(alkylene oxide) of 5 to 20 carbon atoms or bis(lower alkylene) formal.

10. A curable composition according to claim 8 in which R$_1$, R$_2$, R$_7$ and R$_8$ are hydrogen or alkyl of 2 to 18 carbon atoms and R' is the residue of an organic diisocyanate.

11. A method for making a cured polyurethane product which comprises mixing (a) an isocyanate-terminated polyurethane prepolymer with (b) a compound of formula

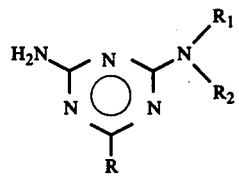

where R is

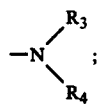

—S—R$_5$—O—R$_6$ or

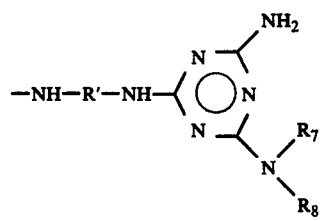

where at least one of R$_1$, R$_2$, R$_3$ and R$_4$ is hydrogen R$_1$, R$_2$, R$_3$, R$_4$, R$_5$, R$_6$, R$_7$ and R$_8$ each independently is hydrogen or an optionally substituted aliphatic or aromatic group, provided however that said aliphatic or aromatic groups are not substituted by hydroxy, and that R$_1$, R$_2$, R$_3$, R$_4$, R$_5$ and R$_6$ may not have ethylenic >C=C< bonds; R' is the divalent residue of an organic diamine, the residue of an organic diisocyanate, or the residue of an organic diepoxide, and where all of R$_1$, R$_2$, R$_3$, R$_4$, R$_5$ and R$_6$ are not all simultaneously hydrogen provided however when R is

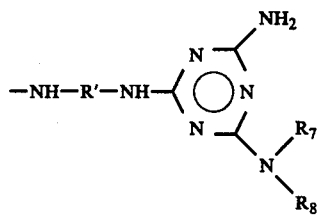

that R$_1$, R$_2$, R$_7$ and R$_8$ can all be hydrogen, that R$_1$ and R$_2$ may contain ethylenic >C=C< bonds; and that if either member of the pairs R$_1$, R$_2$ or R$_7$, R$_8$ contains ethylenic >C=C< bonds, the other member of the same pair must be hydrogen; and heating the mixture.

12. A cured polyurethane product containing the residue of a compound of formula

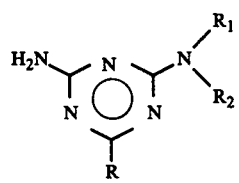

where R is

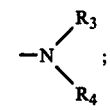

—S—R$_5$—O—R$_6$ or

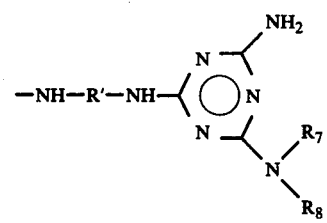

where at least one of R$_1$, R$_2$, R$_3$ and R$_4$ is hydrogen R$_1$, R$_2$, R$_3$, R$_4$, R$_5$, R$_6$, R$_7$ and R$_8$ each independently is hydrogen or an optionally substituted aliphatic or aromatic group, provided that said aliphatic or aromatic groups are not substituted by hydroxy, and that R$_1$, R$_2$, R$_3$, R$_4$, R$_5$ and R$_6$ may not have ethylenic >C=C< bonds; R' is the divalent residue of an organic diamine, the residue of an organic diisocyanate, or the residue of an organic diepoxide, and where all of R$_1$, R$_2$, R$_3$, R$_4$, R$_5$ and R$_6$ are not all simultaneously hydrogen provided however when R is

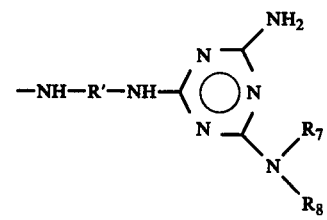

that R$_1$, R$_2$, R$_7$ and R$_8$ can all be hydrogen, that R$_1$ and R$_2$ may have ethylenic >C=C< bonds; and that if either member of the pairs R$_1$, R$_2$ or R$_7$, R$_8$ contains ethylenic >C=C< bonds, the other member of the same pair must be hydrogen.

13. A urethane elastomer comprising the reaction product of an excess of an organic diisocyanate, a material selected from polyester polyols, polyester amide polyols and polyether polyols and a compound of formula

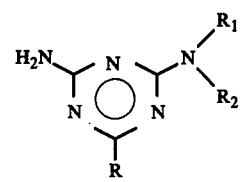

where R is

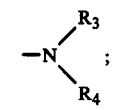

—S—R$_5$—O—R$_6$ or

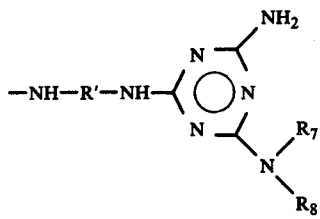

where at least one of $R_1$, $R_2$, $R_3$ and $R_4$ is hydrogen $R_1$, $R_2$, $R_3$, $R_4$, $R_5$ and $R_6$ each independently is hydrogen or an optionally substituted aliphatic or aromatic group, provided that said aliphatic or aromatic groups are not substituted by hydroxyl, and that $R_1$, $R_2$, $R_3$, $R_4$, $R_5$ and $R_6$ may not have ethylenic $>C=C<$ bonds; R' is the divalent residue of an organic diamine, the residue of an organic diepoxide, and where all of $R_1$, $R_2$, $R_3$, $R_4$, $R_5$ and $R_6$ are not all simultaneously hydrogen provided however when R is

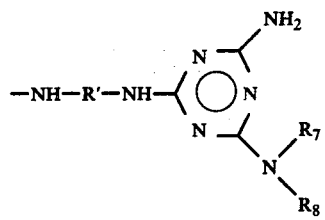

that $R_1$, $R_2$, $R_7$ and $R_8$ can all be hydrogen, that $R_1$ and $R_2$ may have ethylenic $>C=C<$ bonds; and that if either member of the pairs $R_1$, $R_2$ or $R_7$, $R_8$ contains ethylenic $>C=C<$ bonds, the other member of the same pair must be hydrogen.

* * * * *